(12) United States Patent
Lee et al.

(10) Patent No.: US 11,324,706 B2
(45) Date of Patent: May 10, 2022

(54) COMPOSITION FOR INHIBITING GROWTH OF BREAST CANCER STEM CELLS CONTAINING PHENYLACETALDEHYDE

(71) Applicant: JEJU NATIONAL UNIVERSITY INDUSTRY-ACADEMIC COOPERATION FOUNDATION, Jeju-si (KR)

(72) Inventors: Dong Sun Lee, Jeju-si (KR); Hack Sun Choi, Jeju-si (KR); Dong Kee Jung, Jeju-si (KR)

(73) Assignee: JEJU NATIONAL UNIVERSITY-ACADEMIC COOPERATION FOUNDATION, Jeju (KR)

( * ) Notice: Subject to any disclaimer, the term of this patent is extended or adjusted under 35 U.S.C. 154(b) by 0 days.

(21) Appl. No.: 16/097,307

(22) PCT Filed: Apr. 25, 2017

(86) PCT No.: PCT/KR2017/004356
§ 371 (c)(1),
(2) Date: Oct. 29, 2018

(87) PCT Pub. No.: WO2017/188690
PCT Pub. Date: Nov. 2, 2017

(65) Prior Publication Data
US 2020/0188329 A1 Jun. 18, 2020

(30) Foreign Application Priority Data

Apr. 29, 2016 (KR) ........................ 10-2016-0053080

(51) Int. Cl.
| | | |
|---|---|---|
| A61K 31/11 | (2006.01) | |
| A61P 35/00 | (2006.01) | |
| A23L 33/10 | (2016.01) | |
| A61Q 13/00 | (2006.01) | |
| A61Q 19/00 | (2006.01) | |
| A61K 8/33 | (2006.01) | |
| A61K 35/00 | (2006.01) | |

(52) U.S. Cl.
CPC .............. *A61K 31/11* (2013.01); *A23L 33/10* (2016.08); *A61K 8/33* (2013.01); *A61P 35/00* (2018.01); *A61Q 13/00* (2013.01); *A61Q 19/00* (2013.01); *A23V 2002/00* (2013.01)

(58) Field of Classification Search
CPC ........ A61K 31/11; A61Q 13/00; A61Q 19/00; A61P 35/00
See application file for complete search history.

(56) References Cited

U.S. PATENT DOCUMENTS 5,306,707 A * 4/1994 Burrell ..................... A61K 8/35
512/2

FOREIGN PATENT DOCUMENTS

| JP | 2013-510143 | 3/2013 |
|---|---|---|
| KR | 10-1289033 | 7/2013 |
| KR | 10-2015-0136001 | 12/2015 |
| KR | 10-1724541 | 4/2017 |
| WO | 2010-059711 | 5/2010 |

OTHER PUBLICATIONS

Phenylacetaldehyde Safety Data Sheet (Vigon, 2020, 10 pages) (Year: 2020).*
Zheng, Z.-P. et al., "A Phenylacetaldehyde-flavonoid Adduct, 8-C-(E-phenylethenyl)-norartocarpetin, Exhibits Intrinsic Apoptosis and MAPK Pathways-related Anticancer Potential on HepG2, SMMC-7721 and QGY-7703", Food Chemistry, 2016, vol. 197, pp. 1085-1092.
Jemal, A. et al., "Global cancer statistics", CA Cancer J Clin, Mar. 2011, vol. 61, No. 2, pp. 69-90, abstract only.
Al-Hajj, M et al., "Prospective identification of tumorigenic breast cancer cells", Proc Natl Acad Sci USA, 2003, vol. 100, No. 7, pp. 3983-3988, abstract only.
Diehn, M. et al., "Association of reactive oxygen species levels and radioresistance in cancer stem cells", Nature, 2009, vol. 458, No. 7239, pp. 780-783, abstract only.
Choi, H. S. et al., "Transcriptional regulation of mouse mu opioid receptor gene: Sp3 isoforms (M1, M2) function as repressors in neuronal cells to regulate the mu opioid receptor gene", Mol Pharmacol, 2005, vol. 67, No. 5, pp. 1674-1683, abstract only.
Shi, X. et al., "Reactive oxygen species in cancer stem cells", Antioxid Redox Signal, 2012, vol. 16, No. 11, pp. 1215-1228, abstract only.
Sansone, P. et al., "IL-6 triggers malignant features in mammospheres from human ductal breast carcinoma and normal mammary gland", J Clin Invest., 2007, vol. 117, No. 12, pp. 3988-4002, abstract only.

* cited by examiner

*Primary Examiner* — James D. Anderson
(74) *Attorney, Agent, or Firm* — Lex IP Meister, PLLC

(57) ABSTRACT

Disclosed are a composition and a perfume composition for inhibiting growth of breast cancer stem cells containing phenylacetaldehyde or a pharmaceutically acceptable salt thereof as an active (effective) ingredient, and a pharmaceutical composition, a food composition or the like for inhibiting metastasis of breast cancer, or treating or preventing breast cancer, including the composition. The phenylacetaldehyde inhibits growth of breast cancer cells and formation of breast cancer stem cells. In addition, the phenylacetaldehyde inhibits expression of self-renewal genes such as Nanog, Sox2, Oct4, and CD44 known to be specifically expressed in breast cancer stem cells, inhibits production of IL-6 known to be involved in formation of mammospheres of breast cancer stem cells, and inhibits STATS signaling pathways. Accordingly, the compound inhibits growth of breast cancer stem cells and is useful for the treatment of breast cancer.

1 Claim, 25 Drawing Sheets
Specification includes a Sequence Listing.

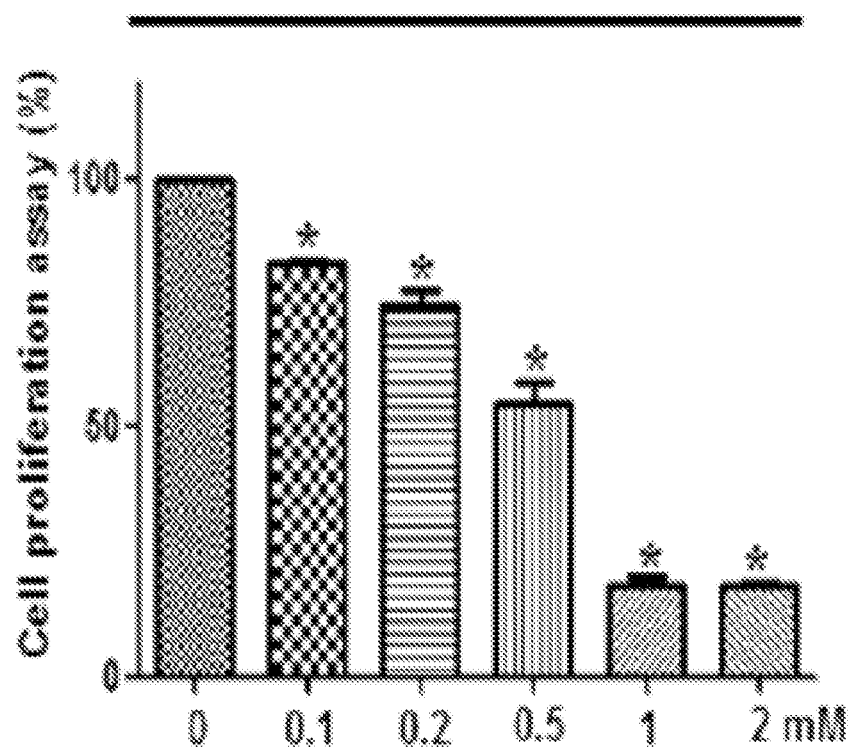

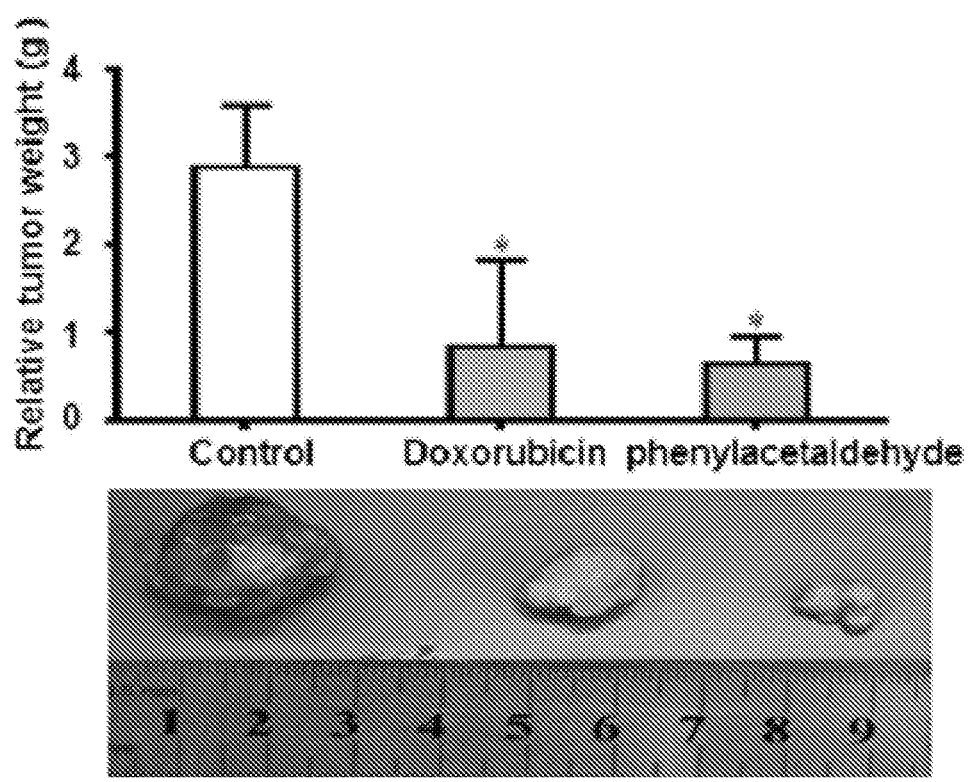

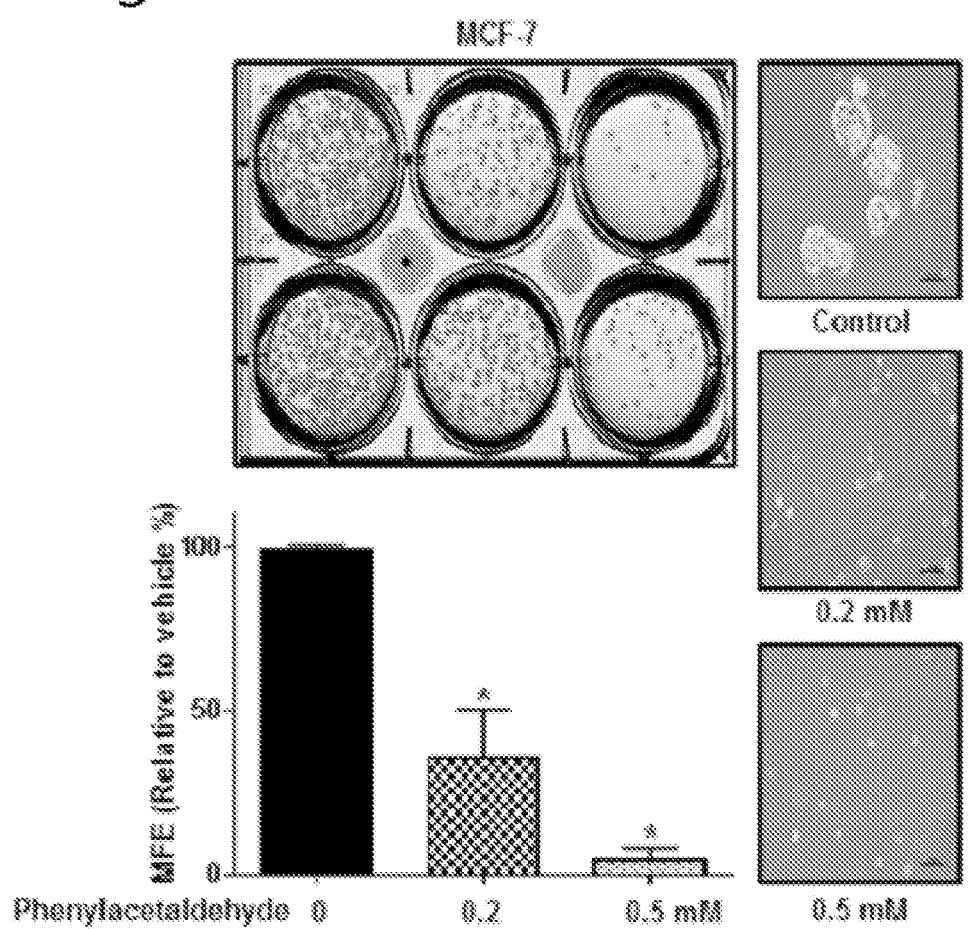

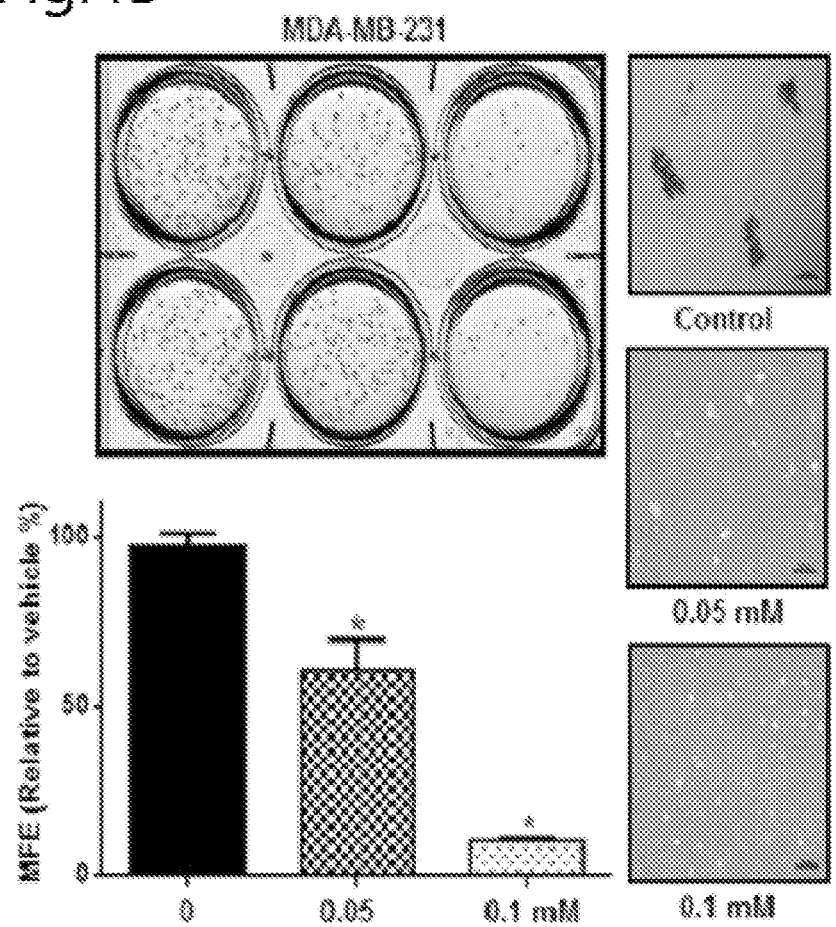

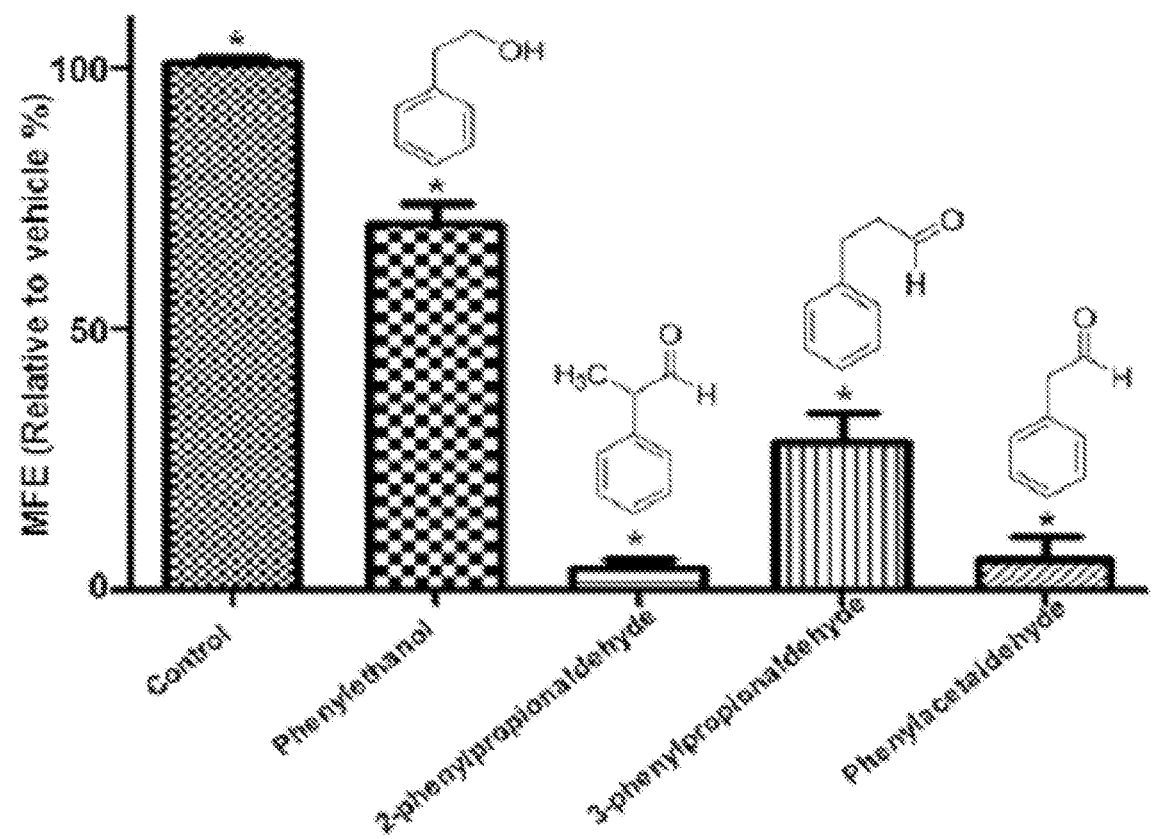

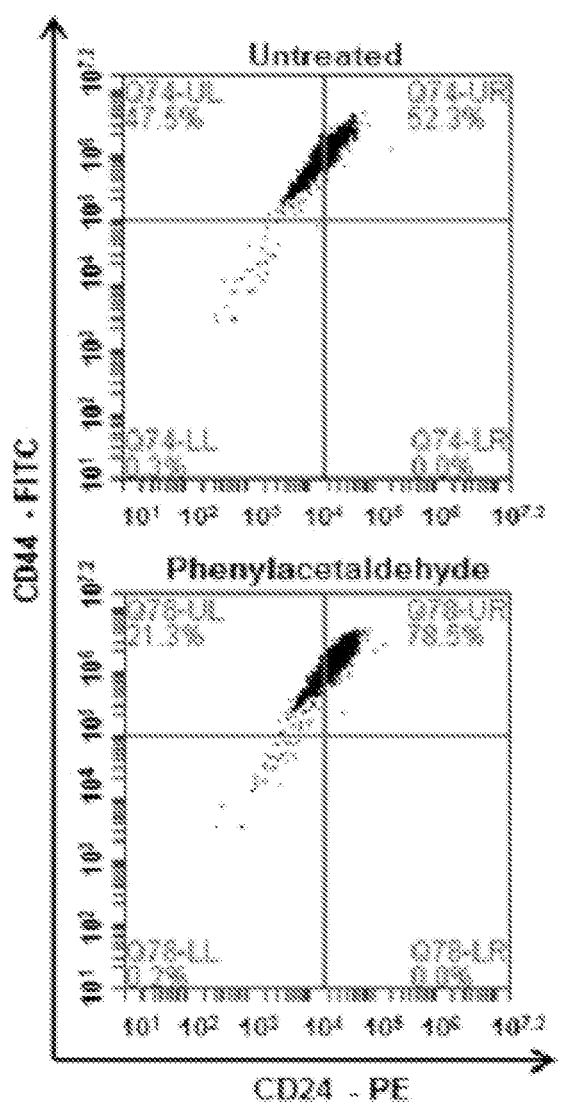

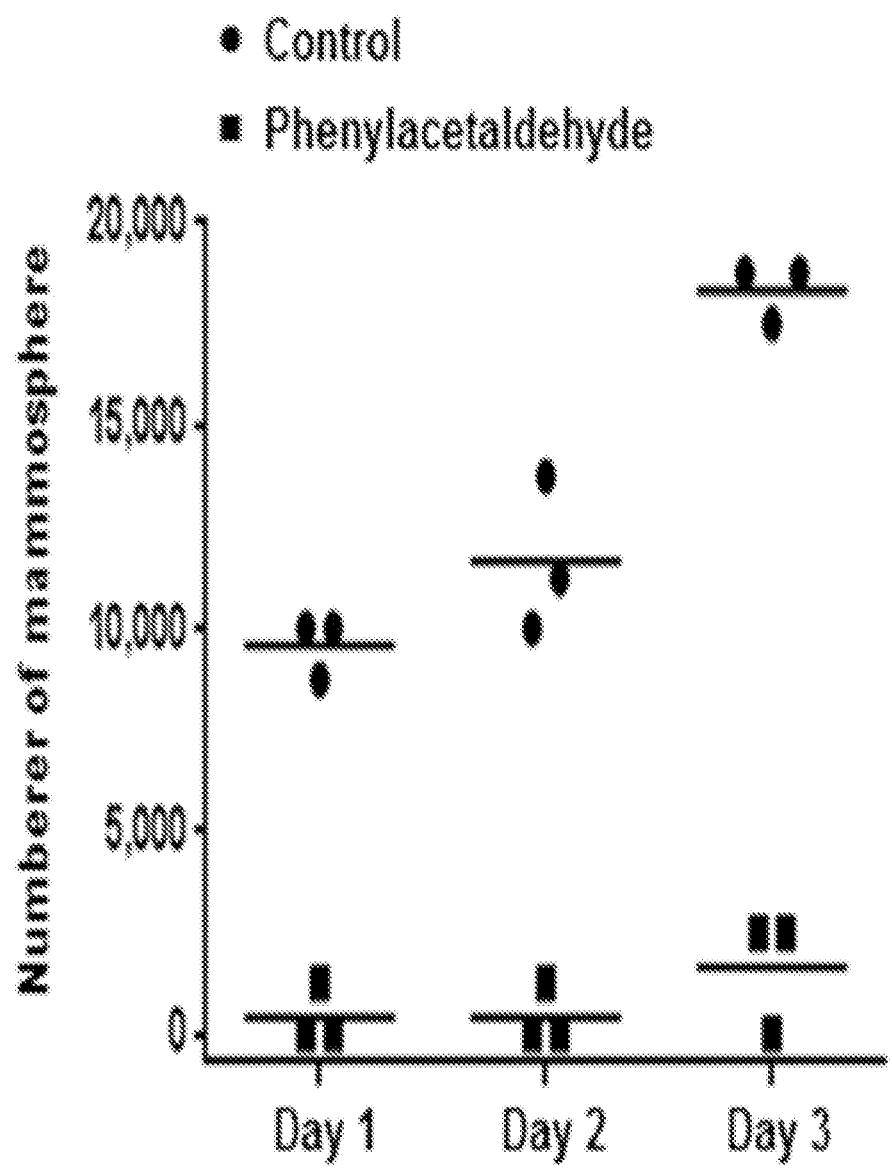

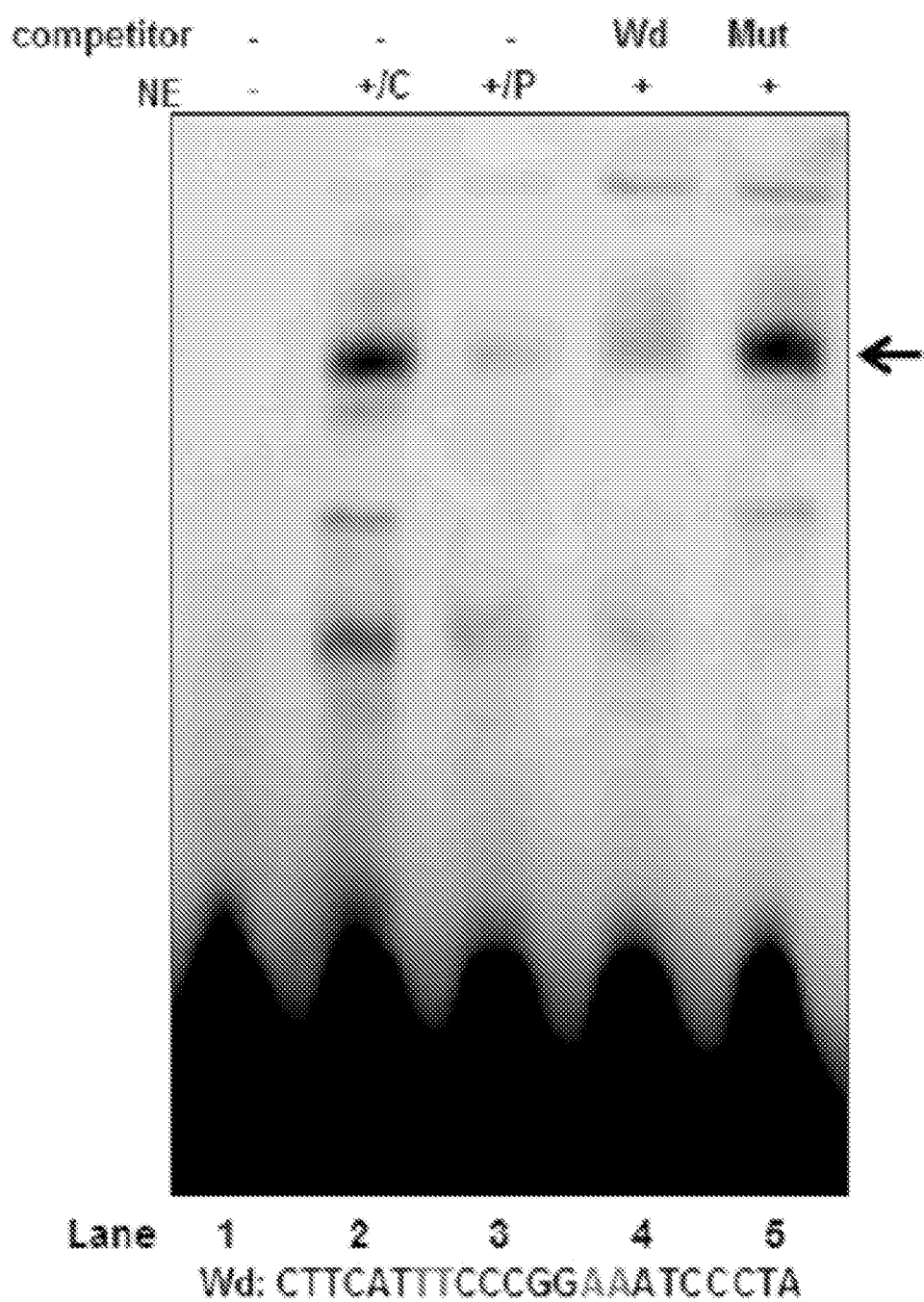

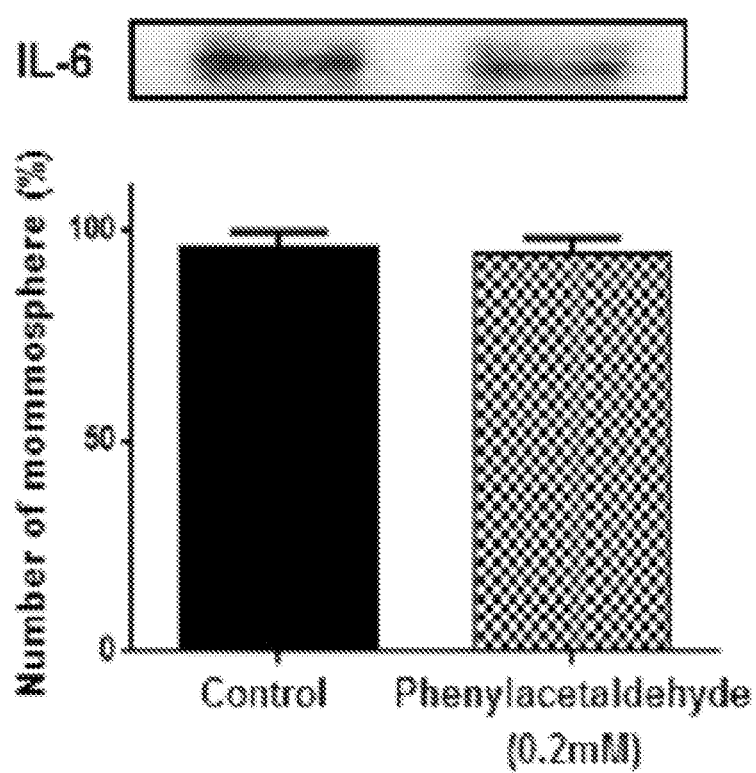

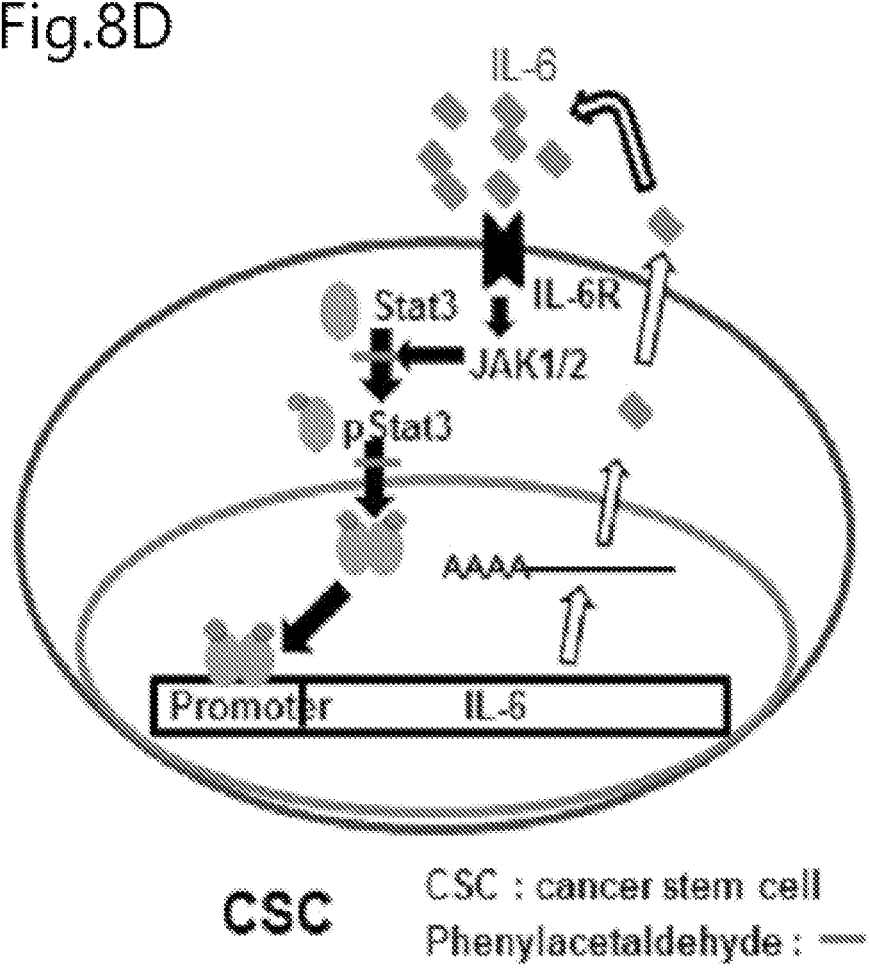

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: CD44 forward primer

<400> SEQUENCE: 1
agaaggtgtg ggcagaagaa                                               20

<210> SEQ ID NO 2
<211> LENGTH: 20
<212> TYPE: DNA
<213> ORGANISM: Artificial Sequence
<220> FEATURE:
<223> OTHER INFORMATION: CD44 reverse primer

<400> SEQUENCE: 2
aaatgcacca tttcctgaga                                               20

<210> SEQ ID NO 3
<211> LENGTH: 20
<212> TYPE: DNA
<213> ORGANISM: Artificial Sequence
<220> FEATURE:
<223> OTHER INFORMATION: NANOG forward primer

<400> SEQUENCE: 3
atgcctcaca cggagactgt                                               20

<210> SEQ ID NO 4
<211> LENGTH: 20
<212> TYPE: DNA
<213> ORGANISM: Artificial Sequence
<220> FEATURE:
<223> OTHER INFORMATION: NANOG reverse primer

<400> SEQUENCE: 4
aagtgggttg tttgcctttg                                               20

<210> SEQ ID NO 5
<211> LENGTH: 18
<212> TYPE: DNA
<213> ORGANISM: Artificial Sequence
<220> FEATURE:
<223> OTHER INFORMATION: OCT4 forward primer

<400> SEQUENCE: 5
agcaaaaccc ggaggagt                                                 18

<210> SEQ ID NO 6
<211> LENGTH: 21
<212> TYPE: DNA
<213> ORGANISM: Artificial Sequence
<220> FEATURE:
<223> OTHER INFORMATION: OCT4 reverse primer

<400> SEQUENCE: 6
ccacatcggc ctgtgtatat c                                             21

<210> SEQ ID NO 7
<211> LENGTH: 23
<212> TYPE: DNA
<213> ORGANISM: Artificial Sequence

```
<220> FEATURE:
<223> OTHER INFORMATION: SOX2 forward primer

<400> SEQUENCE: 7
ttgctgcctc tttaagacta gga                                          23

<210> SEQ ID NO 8
<211> LENGTH: 20
<212> TYPE: DNA
<213> ORGANISM: Artificial Sequence
<220> FEATURE:
<223> OTHER INFORMATION: SOX2 reverse primer

<400> SEQUENCE: 8
ctggggctca aacttctctc                                              20

<210> SEQ ID NO 9
<211> LENGTH: 20
<212> TYPE: DNA
<213> ORGANISM: Artificial Sequence
<220> FEATURE:
<223> OTHER INFORMATION: Beta-actin forward primer

<400> SEQUENCE: 9
tgttaccaac tgggacgaca                                              20

<210> SEQ ID NO 10
<211> LENGTH: 20
<212> TYPE: DNA
<213> ORGANISM: Artificial Sequence
<220> FEATURE:
<223> OTHER INFORMATION: Beta-actin reverse primer

<400> SEQUENCE: 10
ggggtgttga aggtctcaaa                                              20

<210> SEQ ID NO 11
<211> LENGTH: 22
<212> TYPE: DNA
<213> ORGANISM: Artificial Sequence
<220> FEATURE:
<223> OTHER INFORMATION: biotin-upper strand of Stat3 probe

<400> SEQUENCE: 11
cttcatttcc cggaaatccc ta                                           22

<210> SEQ ID NO 12
<211> LENGTH: 22
<212> TYPE: DNA
<213> ORGANISM: Artificial Sequence
<220> FEATURE:
<223> OTHER INFORMATION: biotin-lower strand of Stat3 probe

<400> SEQUENCE: 12
tagggatttc cgggaaatga ag                                           22
```

COMPOSITION FOR INHIBITING GROWTH OF BREAST CANCER STEM CELLS CONTAINING PHENYLACETALDEHYDE

TECHNICAL FIELD

The present invention relates to a composition and a perfume composition for inhibiting growth of breast cancer stem cells containing phenylacetaldehyde or a pharmaceutically acceptable salt thereof as an active (effective) ingredient, and a pharmaceutical composition, a food composition or the like for inhibiting metastasis of breast cancer or for treating or preventing breast cancer, including the composition.

BACKGROUND ART

Interest in cancer stem cells has emerged as antitumor treatment (chemotherapy) fails to effectively target and treat cell populations in tumors, leading to tumor recurrence and metastasis. Since many cytotoxic anticancer drugs generally target rapidly proliferating cells, slowly proliferating cancer stem cells can survive during cytotoxic chemotherapy. Basal cell phenotype breast cancer is considered to originate from the earliest mammary progenitor cells during differentiation and is known to be poor in prognosis and resistant to conventional chemotherapy. This is a good example to support that the cause for chemotherapy failure is due to failure of the target treatment for cancer stem cells.

Several treatments have been devised based on the cancer stem cell hypothesis. One of the most well-known methods is to use the self-renewal pathway of cancer stem cells. The important point for this treatment is that the self-renewal of only cancer stem cells should be targeted, while maintaining the self-renewal in normal stem cells. For example, the Notch signal is driven by an enzyme called secretase and tumor inhibitory effects can be obtained when using a secretase inhibitor for Notch1-overexpressed breast cancer. According to a recent report, even when targeting the Hedgehog signaling system, an anticancer effect can be obtained. The tumor was dramatically shrunken, when the hedgehog inhibitor, cyclopamine, was administered to a tumor xenograft animal.

Meanwhile, breast cancer is a common cancer in women and is known to be the leading cause of death in female cancer patients (al A, Bray F, Center M M, Ferlay J, Ward E and Forman D. Global cancer statistics. CA Cancer J Clin. 2011; 61(2):69-90). Breast cancer is still known to be the most dangerous disease due to recurrence and metastasis, although polychemotherapy in early breast cancer and extensive mammograms and adjuvant therapies with tamoxifen have reduced the mortality rate of breast cancer. Cancer stem cells (CSCs) were first identified in myeloid leukemia and subsequently found in a variety of solid cancer populations including breast, brain, colon, ovary, pancreas and prostate cancer. The cancer stem cells may be called "tumor-initiating cells" and "cancer stem-like cells". In addition, it has been shown that a variety of types of cancer including breast cancer are derived from cancer stem cells (CSCs), which is a small group of tumors. Such a group is known to induce changes in tumor volumes through self-renewal and differentiation. Shh (Sonic hedgehog), Stat3, NF-κB, Wnt/β-catenin, TGF-β and Notch signaling pathways are known to be critical for the self-renewal of CSCs.

Cancer stem cells exhibit drug resistance and radiation resistance to chemotherapy and radiation therapy, and cause cancer recurrence and metastasis. Therefore, target therapy for cancer stem cells is essential for cancer treatment. Cancer stem cells are known to express certain proteins including Oct4, Sox2, Nanog and aldehyde dehydrogenase-1 (ALDH). ALDH is an enzyme that oxidizes genetic toxic aldehyde and its enzyme activity is widely used as a CSC marker for leukemia, head and neck, bladder, bone, colon, liver, lung, pancreas, prostate, thyroid and cervical cancer. ALDH is known as a therapeutic target for cancer stem cells. In addition, it is known that the clinical sample has excellent ability to form tumors in the breast cancer group expressing $CD44^{high}/CD24^{low}$ (Al-Hajj M, Wicha M S, Benito-Hernandez A, Morrison S J and Clarke M F. Prospective identification of tumorigenic breast cancer cells. Proc Natl Acad Sci USA. 2003; 100(7):3983-3988).

Stat3 (Signal transducer and activator of transcription 3) is generally activated in CSCs and formation of mammospheres relates to JAK1/2-STAT3 pathways. Secreted IL-6 activates JAK1/2-STAT3 pathways and promotes expression of Oct4 genes. IL-6/JAK1/2/STAT3 signaling pathways are known to be important for conversion of NSCCs into CSCs. It is known that, when STATS signaling pathways are blocked, growth of breast cancer cell-derived $CD44^{high}/CD24^{low}$-stem cell-like cells is inhibited. NF-κB (nuclear factor-κB) transcription factors are structurally (regularly) activated in tumor cells including colon, breast and liver cancer, and are controlled by IκB kinase (IKK) complexes. The specific inhibitor of NF-κB, pyrrolidine dithiocarbamate (PDTC), is known to inhibit breast cancer stem-like cells.

The breast cancer stem cells are known to be identified by expression of bio-markers such as $CD44^{high}/CD24^{low}$, $ESA^+$ (epithelial-specific antigen) and ALDH1. Anticancer chemotherapy is known to increase the percentage of cancer cells expressing $CD44^{high}/CD24^{low}$ and formation of mammospheres. CSCs induce increases in levels of specific ABC transporters to protect CSCs from toxins. ABC pumps may be used to separate side population (SP) and may be classified by ABCG2 transporter-specific Hoechst 33342 dyes. Breast CSCs produce low levels of reactive oxygen species as compared to tumor cells, and breast cancer stem-like cells are resistant to radiation. The reason for this is that, since ROSs are main mediators of ionized radiation-induced apoptosis, CSCs have less DNA damage than non-stem cancer cells (Diehn M, Cho R W, Lobo N A, Kalisky T, Dorie M J, Kulp A N, Qian D, Lam J S, Ailles L E, Wong M, Joshua B, Kaplan M J, Wapnir I, Dirbas F M, Somlo G, Garberoglio C, et al. Association of reactive oxygen species levels and radioresistance in cancer stem cells. Nature. 2009; 458 (7239):780-783).

The breast cancer cell line, MCF-7, is known to have a partial colony of cells having a similar ability to stem cells that can grow into elliptical cells, rather than undergoing apoptosis in vitro without adherence. When the condition of the absence of the substratum is artificially created by suspension culture, cells having the same properties as stem cells attach to one another to form spherical cell clusters, and these cell clusters are called "neurospheres". Human breast stem cells, to which this concept is applied, are called "mammospheres". Mammospheres have 8 times as many progenitor cells as normal human breast cells and can be continuously passage-cultured. After several passages, 100% of the cells grow into bipotent progenitors. The mammospheres can be differentiated into adult breast cells, i.e., mammary gland epithelial cells, ductal epithelial cells and alveolar epithelial cells, and are observed to form a three-dimensional complex functional breast structure in Matrigel. The mammospheres have the self-propagation ability, which is one of the most characteristic features of stem cells, so that several mammospheres or breast stem cells can be obtained at great amounts from one mammosphere. Mammospheres are reported to be actual breast stem cells, since it is also identified that many expression genes are overlapped as compared to hematopoietic stem cells, neural stem cells, embryonic stem cells and the like. The standard method of analyzing such self-renewal ability of cancer stem cells is to analyze in vivo transplantation and in vitro mammosphere formation.

DISCLOSURE

Technical Problem

To date, research on cancer stem cells has been greatly limited and their roles in the formation and maintenance of tumors have not been clearly found. In order to efficiently conduct treatment targeting only cancer stem cells without damaging normal stem cells, knowledge and understanding regarding molecular biological characteristics and regulations pathways thereof, which are important for maintenance and regulation of cancer stem cells, are needed.

Until now, there has been almost no research on anticancer drugs and natural product-derived extracts that directly target cancer stem cells. There have been conventional techniques focusing on inhibition of cancer stem cells by directly inhibiting the target genes of the cancer stem cells or by inhibiting upstream signal transduction proteins of the cancer stem cells. However, there was much difficulty in targeting these genes due to mutations in oncogenes or proteins in many tumor patients.

Technical Solution

In accordance with the present invention, the above and other objects can be accomplished by the provision of a composition for inhibiting growth of breast cancer stem cells containing a compound represented by Formula 1 or a pharmaceutically acceptable salt thereof as an active ingredient.

In another aspect of the present invention, provided is a pharmaceutical composition for inhibiting metastasis of breast cancer, or for treating or preventing breast cancer, including the composition for inhibiting growth of breast cancer stem cells.

In another aspect of the present invention, provided is a food composition for inhibiting metastasis of breast cancer or for alleviating or preventing breast cancer, including the composition for inhibiting growth of breast cancer stem cells.

In another aspect of the present invention, provided is a perfume composition for inhibiting growth of breast cancer stem cells, containing the volatile compound represented by Formula 1.

In another aspect of the present invention, provided are a pharmaceutical composition, a skin preparation for external use, a food composition, a cosmetic composition, a personal care product, a home care product, an air freshener composition, an additive for humidifiers, a cigarette filter and an electronic cigarette, each including the perfume composition.

In another aspect of the present invention, provided is a method for inhibiting growth of breast cancer stem cells including exposing the volatile compound represented by Formula 1 to breast cancer stem cells of a subject.

In another aspect of the present invention, provided is a method for inhibiting growth of breast cancer stem cells including administering the compound represented by Formula 1 or a pharmaceutically acceptable salt thereof to a subject.

In another aspect of the present invention, provided is a method for inhibiting metastasis of breast cancer including administering the compound represented by Formula 1 or a pharmaceutically acceptable salt thereof to a subject.

In another aspect of the present invention, provided is a method for preventing or treating breast cancer including administering the compound represented by Formula 1 or a pharmaceutically acceptable salt thereof to a subject.

In another aspect of the present invention, provided is use of the compound represented by Formula 1 or a pharmaceutically acceptable salt thereof for the production of a drug for inhibiting growth of breast cancer stem cells.

In another aspect of the present invention, provided is use of the compound represented by Formula 1 or a pharmaceutically acceptable salt thereof for the production of a drug for inhibiting metastasis of breast cancer.

In another aspect of the present invention, provided is use of the compound represented by Formula 1 or a pharmaceutically acceptable salt thereof for the production of a drug for preventing or treating breast cancer.

Advantageous Effects

The phenylacetaldehyde according to the present invention inhibits growth of breast cancer cells and formation of breast cancer stem cells. In addition, the phenylacetaldehyde inhibits expression of self-renewal genes such as Nanog, Sox2, Oct4, and CD44 known to be specifically expressed in breast cancer stem cells, inhibits production of IL-6 known to be involved in formation of mammospheres of breast cancer stem cells, and inhibits STATS signaling pathways. Accordingly, the compound inhibits growth of breast cancer stem cells and is useful for the treatment of breast cancer.

BRIEF DESCRIPTION OF THE DRAWINGS

The above and other objects, features and other advantages of the present invention will be more clearly understood from the following detailed description taken in conjunction with the accompanying drawings, in which:

FIGS. 1A to 1F show that PAA inhibits a variety of cancer characteristics in breast cancer cell lines.

(FIGS. 1A, B and C) show chemical structures of PAA and viability of MCF-7 and MDA-MB-231 cells depending on PAA. MCF-7 and MDA-MB-231 cells were treated with increasing concentrations of PAA for 48 hours. Anti-proliferation effects of PAA were measured by MTS analysis.

(FIGS. 1D, E and F) show effects of PAA on apoptosis of breast cancer cells. MDA-MB-231 cells were treated with PAA for 24 hours, and apoptotic cells were analyzed by FACS using an Annexin V-PI staining kit. Caspase 3/7 activity in MDA-MB-231 cells was analyzed using a Caspase-Gloss 3/7 kit. By fluorescent staining, apoptotic cells were analyzed and nuclei thereof were stained with Hoechst 33258 in breast cancers (magnified, 200×) (FIG. 1);

(FIG. 2A) shows effects of PAA on migration potential of human breast cancer cells. Scratch curing of MDA-MB-231 cells was imaged at 0 and 18 hours with or without PAA treatment;

(FIG. 2B) shows effects of PAA on colony formation in human breast cancer cells. The dissociated 1,000 MDA-MB-231 cells were seeded on a 6-well plate and treated with marked concentrations of PAA and DMSO for 7 days. A representative image of colonies was recorded. Shown data is represented as a mean±SD in three independent tests. * means P<0.05, as compared to DMSO-treated control group;

FIGS. 3A, 3B and 3C show effects of PAA on tumor growth in xenograft tumor models. 3 million cells were injected into breast fat pads of NOD-SCID female nude mice;

FIG. 3A shows effects of PAA and Dox on tumor growth in immunodeficient nude mice producing MCF-7 cells. The dose of used drug is 10 mg/kg. 9 weeks later, the image was captured with Odyssey® image (LICOR, Pearl image system, USA). Using an IRDye 800 CW optical probe (2DG), a high grade of tumor was used to detect breast tumors at a channel of 800 nm and was represented by pseudo-color;

FIG. 3B shows that tumor volume was measured twice a week using a caliper and was calculated in accordance with (width$^2$×length)/2. A tumor growth curve was monitored during the test period;

FIG. 3C shows effects of PAA on weight of tumor. Tumor volume was measured after initiation of treatment. * means p<0.05, as compared to control group. A representative image was captured at the end of 9 weeks of treatment. Results are shown as a vehicle-treated control group, a PAA-treated mouse and a Dox-treated mouse;

FIG. 4 shows effects of PAA on formation of mammospheres. MCF-7 and MDA-MB-231 cells were cultured for 7 days under the condition of mammosphere formation;

FIGS. 4A, 4B and 4C show effects of PAA on formation of MCF-7 cell-derived mammospheres. Primary mammospheres were cultured together with PAA (0.2 and 0.5 mM) or DMSO;

(FIG. 4B) shows effects of PAA on formation of MDA-MB-231 cell-derived mammospheres. The mammospheres were cultured together with PAA (0.05 and 0.1 mM) or DMSO. MCF-7 and MDA-MBB-231 cells were treated with PAA and DMSO during the culture period of 7 days. The image was obtained with a 10× microscope and shows representative mammospheres (scale bar=100 µm);

(FIG. 4C) shows effects of PAA steam (scent) on formation of CSCs. Cancer stem cells were cultured in the presence of PAA steam (1 mM) and vehicle (methanol) for 7 days. An image was obtained with a 10× microscope and showed representative mammospheres (scale bar=100 µm);

FIGS. 5A and 5B show effects of PAA on formation of mammospheres;

(FIG. 5A) shows pathways regarding production of PAA and phenylethanol, volatile compounds derived from tomatoes;

(FIG. 5B) shows effects of PAA and related volatile compounds on formation of mammospheres derived from breast cancer. Shown data is represented as a mean±SD in three independent tests. * means P<0.05, as compared to DMSO-treated control;

FIGS. 6A and 6B show effects of PAA on expression of cancer stem cells markers in breast cancer cell lines;

FIG. 6A shows that MDA-MB-231 cells were treated with PAA (0.1 mM) or DMSO for 2 days and then CD44$^{high}$/CD24$^{low}$ cell populations were analyzed. For FACS analysis, 50,000 cells were obtained. Gating was based on control antibody;

FIG. 6B shows effects of PAA on ALDH-positive cell populations. MDA-MB-231 cells were treated with PAA (0.1 mM) or DMSO, and then subjected to ALDEFLUOR assay and FACS analysis. A top panel represents, as a negative control group, an ALDH-positive cell treated with an ALDH inhibitor, DEAB, and a bottom panel represents an ALDH-positive cell not treated with DEAB. An ALDH-positive population was represented by a box;

FIGS. 7A, 7B, and 7C show effects of PAA on cancer stem cell loads in breast cancers;

FIG. 7A shows that transcriptional expression levels of CSC markers, i.e., Nanog, Sox2, Oct4 and CD44 genes were analyzed by real-time PCR using primers specific to the CSC markers in PAA- and DMSO-treated mammospheres. β-actin was used as an internal control group;

FIG. 7B shows detection of PAA-induced ROSs in MDA-MB-231 cells. ROSs in cells were analyzed using a ROS-Glo™ H$_2$O$_2$ assay kit. PAA induced ROS production of breast cancers;

FIG. 7C shows effects of PAA on growth of mammospheres. PAA inhibits growth of mammospheres. Mammospheres treated with PAA and DMSO for 2 days were separated into single cells and the equal number of cells were seeded on a 6 cm dish. 24 hours after seeding, the cells were counted. At 2- and 3-days, the cells were counted three times and plotted by the mean of the number. The data was represented by mean±standard deviation (SD). * means P<0.05, as compared to DMSO-treated control group;

FIGS. 8A, 8B, 8C and 8D show effects of PAA on STAT3 signaling and protein levels of extracellular IL-6 in mammospheres;

FIG. 8A shows that expression and activation of nuclear proteins of STAT3 and NF-κB in mammospheres were identified by antibodies regarding pStat3, STAT3, p65, Lamin b and β-actin;

FIG. 8B shows EMSA (electrophoretic mobility-shift assay) of PAA-treated MDA-MB-231 cell-derived mammosphere nuclear lysates. Nuclear lysates were cultured in biotin-labeled Stat3 probes and were isolated by 6% PAGE;

Figure 8A:
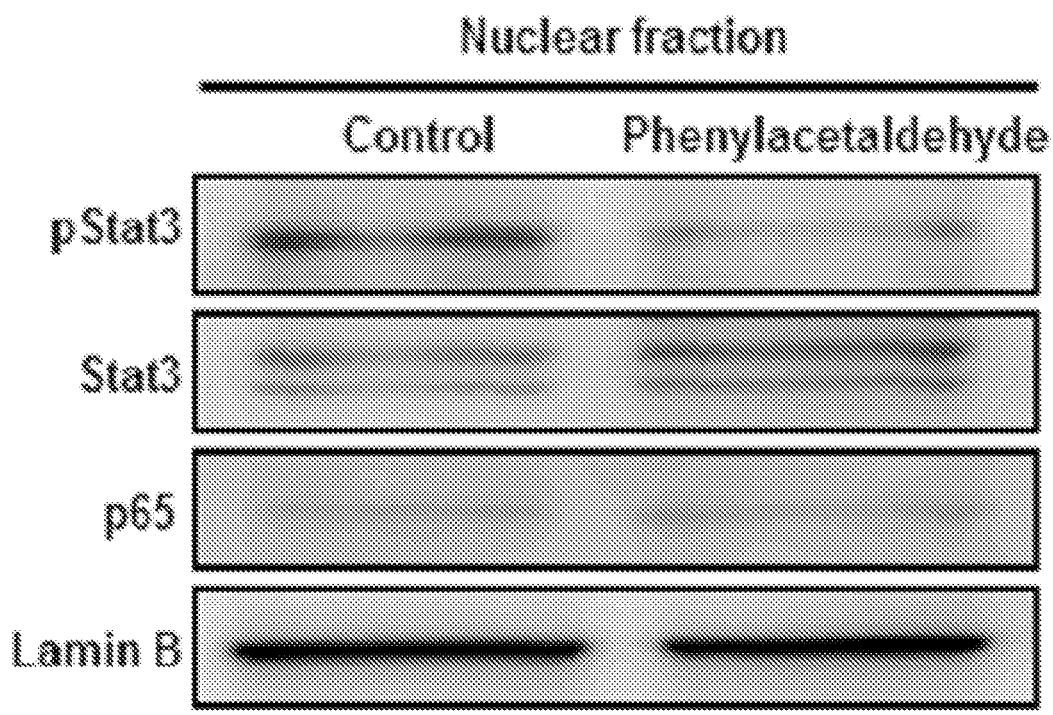
Figure 9:
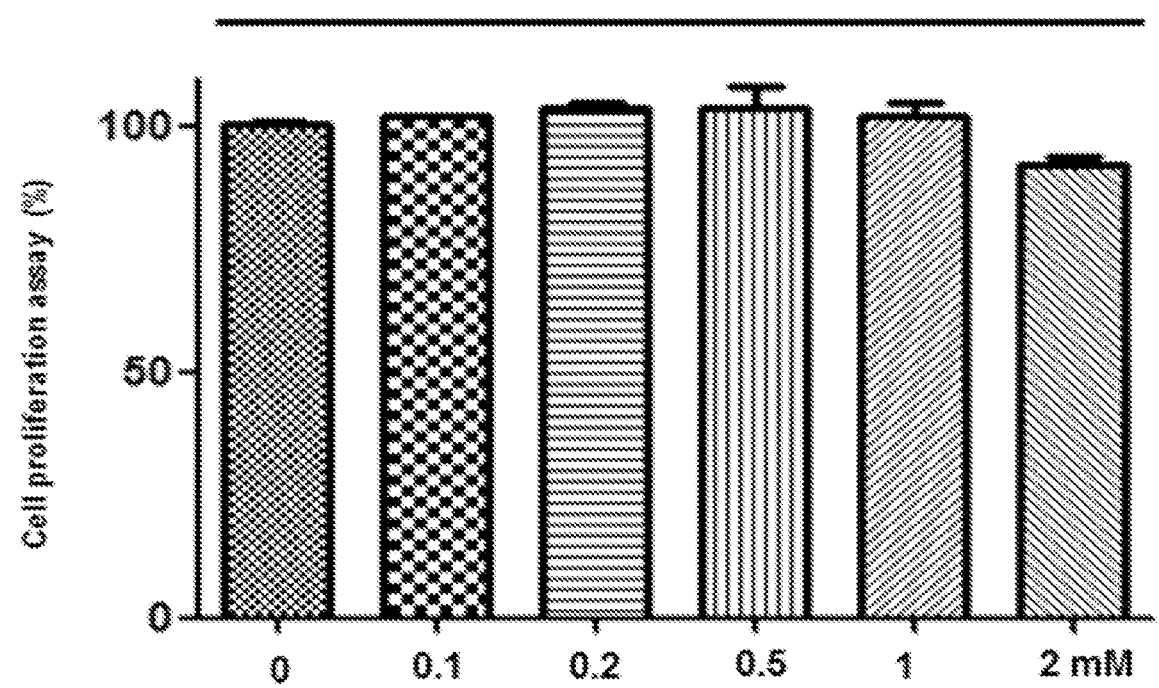

Lane 1: probe alone; Lane 2: probe+nuclear extracts; Lane 3: probe+PAA-treated nuclear extracts; Lane 4: self-competition; Lane 5: nuclear extracts cultured together with mutant STAT3 probe. The PAA reduced DNA/STAT3 interactions in mammosphere nuclear lysates;

FIG. 8C shows immunoblots of mammosphere-derived extracellular fluids cultured with a number of mammospheres and IL-6 antibodies, as an internal control group. PAA reduces extracellular IL-6 protein levels in mammosphere culture;

FIG. 8D shows formation models of CSCs by Stat3 signals and IL-6. Activated pStat3 creates a dimer. The dimerized pStat3 moves to the nucleus and binds to the promoter of IL-6 genes to produce IL-6. The secreted IL-6 converts non-cancer stem cells (NSCCs) into cancer stem cells (CSCs) and regulates dynamic equilibrium from NSCCs to CSCs. PAA relieves regulation of dynamic equilibrium from NSCCs to CSCs through relief of regulation of IL-6 and dephosphorylation of STATS; and FIG. 9 shows that proliferation of HT-29 human colorectal cancer cells is not inhibited.

Anti-proliferation effects of PAA in human colorectal cancer cell lines were measured by MTS analysis. Cells treated with PAA at a concentration up to 2 mM have no significant proliferation inhibitory effects in colorectal cancer cell lines.

BEST MODE

The present inventors tried to identify whether or not phenylacetaldehyde (PAA), which is a volatile compound derived from plants such as roses and tomatoes, can serve as an inhibitor of breast cancer stem cells (CSCs). As a result, they found that PAA can selectively inhibit breast cancer stem cells (CSCs) and suppress the STAT5 signaling pathway in breast cancer-derived mammosphere cells. In addition, they found that PAA effectively inhibits growth of tumors using mouse xenograft models. Accordingly, the present invention was completed based on findings that PAA can inhibit growth of breast cancer stem cells by targeting CSCs and is useful for the treatment of breast cancer.

In order to accomplish the objects mentioned above, the present invention provides a composition for inhibiting growth of breast cancer stem cells containing the following compound represented by Formula 1 or a pharmaceutically acceptable salt thereof as an active ingredient:

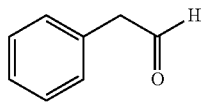

[Formula 1]

According to the present invention, the compound is phenylacetaldehyde (PAA) and is volatile. The compound according to the present invention may be derived from rose or tomato plants and may be a volatile substance of flowers, an insect attractant or a volatile fragrant substance of roses and tomatoes. Phenylacetaldehyde (PAA) is known to be important for flavors of a variety of food. In addition, the composition for inhibiting growth of breast cancer stem cells may further include at least one compound selected from phenylethanol, 2-phenylpropionaldehyde, and 3-phenylpropionaldehyde.

As used herein, the term "cancer" generally represents or describes the physiological condition of a mammal having characteristics of unregulated cell growth.

As used herein, the term "breast cancer stem cell" refers to an undifferentiated cell that can be differentiated into breast cancer cells.

As used herein, the term "inhibition of growth of breast cancer stem cells" means inhibition of maintenance of breast cancer stem cells, inhibition of malignance of breast cancer stem cells, inhibition of migration of breast cancer stem cells and invasive inhibition of breast cancer stem cells.

In one embodiment of the present invention, in order to identify whether or not PAA can inhibit growth of breast cancer stem cells, primary mammospheres derived from MCF-7 and MDA-MB-231 cells were treated with PAA. As a result, it was identified that PAA inhibits formation of primary mammospheres derived from breast cancer cell lines. Specifically, it was identified that the number of mammospheres derived from breast cancer cells, i.e., MCF-7 cells, is decreased to 50 to 90% and the size of mammospheres is decreased (FIG. 4A). In addition, treatment with PAA causes a decrease in the number of primary mammospheres derived from other breast cancer cells, i.e., MDA-MB-231 cells as well (FIG. 4B). Accordingly, the compound of the present invention can suppress formation or growth of mammospheres.

In addition, in one embodiment of the present invention, it is identified that, in addition to a phenylalanine-derived volatile materials, i.e., PAA and phenylethanol, and structural analogs, i.e., 2-phenylpropionaldehyde and 3-phenylpropionaldehyde, inhibit formation of primary mammospheres derived from MCF-7 cells (FIG. 5B).

According to the present invention, the breast cancer stem cells may express at least one self-renewal gene selected from Nanog, Sox2, Oct4, and CD44. In one embodiment of the present invention, phenylacetaldehyde suppresses self-renewal genes such as Nanog, Sox2, Oct4 and CD44 known to be expressed specifically in breast cancer stem cells (FIG. 7A), inhibits production of IL-6 involved in formation of mammospheres of breast cancer stem cells (FIG. 8C), and inhibits signaling pathways of STAT5 (FIG. 8B). Accordingly, the compound can inhibit growth of breast cancer stem cells.

The composition of the present invention may be used as a pharmaceutical composition or a food composition.

When the composition of the present invention is used as a pharmaceutical composition, it can contain the compound or a pharmaceutically acceptable salt thereof.

As used herein, the term "pharmaceutically acceptable salt" refers to any salt that has biological and/or physiological activity of the compound and minimizes undesired toxicologic effects, and means a salt prepared in accordance with a method ordinarily used in the corresponding technical field and this preparation method is well-known in the art. Specifically, the pharmaceutically acceptable salt includes salts derived from inorganic and organic acids and bases, which are pharmacologically or physiologically acceptable, but is not limited thereto.

For example, pharmaceutically acceptable base addition salts may be prepared from inorganic and organic bases. The salts derived from inorganic bases may include, but are not limited to, sodium, potassium, lithium, ammonium, calcium and magnesium salts. The salts derived from organic bases may include, but are not limited to: primary, secondary and tertiary amines; substituted amines including naturally derived substituted amines; and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylene diamine, glucosamine, N-alkyl glucamine, theobromine, purine, piperazine, piperidine, and/or N-ethyl piperidine. In addition, other carboxylic acid derivatives, for example, carboxylic acid amides including carboxamides, lower alkyl carboxamides, di(lower alkyl) carboxamides and the like may be included.

For example, pharmaceutically acceptable acid addition salts may be prepared from inorganic and organic acids. Salts derived from inorganic acids include hydrochloric acid, bromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and/or salicylic acid and the like, but are not limited thereto.

According to the present invention, the pharmaceutical composition may contain a pharmaceutically acceptable carrier or additive. As used herein, the term "pharmaceutically acceptable" means having no toxicity that renders a subject to be applied (prescribed) to be inadaptable, while not inhibiting activity of an active ingredient. The term "carrier" is defined as a compound that facilitates incorporation of a compound into cells or tissues.

The phenylacetaldehyde according to the present invention may be administered alone or in combination with any convenient carrier or the like. Such an administration formulation may be a formulation for single or multiple administration. The pharmaceutical composition may be a solid or liquid formulation. Examples of solid preparation include powders, granules, tablets, capsules, suppositories and the like, but are not limited thereto. Examples of solid preparation include carriers, flavoring agents, binders, preservatives, disintegrants, lubricants, fillers and the like, but are not limited thereto. Examples of the liquid preparation include water, solutions such as propylene glycol solutions, suspensions, emulsions and the like, but are not limited thereto. The liquid preparation may be prepared by adding suitable colorants, flavors, stabilizers, tackifiers and the like. For example, powders may be prepared by simply mixing PAA, which is the active ingredient of the present invention, with pharmaceutically acceptable suitable carriers such as lactose, starch and microcrystalline cellulose. The granules may be prepared by mixing the PAA of the present invention, pharmaceutically acceptable suitable carriers, and pharmaceutically acceptable suitable binders such as polyvinylpyrrolidone, hydroxypropylcellulose, and then subjecting to wet-granulation using a solvent such as water, ethanol or isopropanol, or dry-granulation using a compression force. In addition, the tablets may be prepared by mixing the granules with a pharmaceutically acceptable suitable lubricant such as magnesium stearate and tableting using a tablet press machine.

The phenylacetaldehyde of the present invention may be administered in the form of, for example, an oral preparation, an injection preparation (for example, intramuscular injection, intraperitoneal injection, intravenous injection, infusion, subcutaneous injection or implant), an inhalant, a nasal preparation, a vaginal preparation, a rectal preparation, a sublingual preparation, a transdermal preparation, a topical preparation or the like, depending on the conditions of the disease or subject in need of treatment, but is not limited thereto. Depending on the administration route, the phenylacetaldehyde of the present invention may be formulated into a suitable administration unit formulation containing a commonly used, nontoxic and pharmaceutically acceptable carrier, additive or vehicle.

The pharmaceutical composition of the present invention may be administered in a daily dose of about 0.0001 mg/kg to about 10 g/kg, preferably, about 0.001 mg/kg to about 1 g/kg. However, the dose may be changed depending on purification degree of the mixture, conditions of patient (age, gender, body weight or the like), severity of pathology to be treated, and the like. If needed, the total daily dose may be administered portionwise for one day for convenience.

When the composition of the present invention is used as a pharmaceutical composition, regarding the content of PAA in the composition, an effective amount providing anti-inflammatory activity can be suitably controlled depending on symptoms of the disease, the progression of the symptoms, conditions of the patient and the like. For example, the amount of PAA may be, based on the total weight of the composition, 0.0001% by weight or more, specifically, 0.001% by weight or more, and 80% by weight or less, specifically, 50% by weight or less, but is not limited thereto.

In addition, it is found that the compound of the present invention inhibits growth of breast cancer cell-derived mammospheres and is useful as a food composition for inhibiting growth of breast cancer stem cells.

When the composition of the present invention is used as a food composition, it may include an acceptable food auxiliary additive, and may further include a suitable carrier, excipient and diluent commonly used in the production of food.

As used herein, the term "food" means a natural or processed product containing one or more nutrients and specifically means a ready-to-eat product that is processed to some extent. Commonly, food is intended to cover a variety of food, functional food, beverages, food additives and beverage additives. Examples of the food include a variety of food, beverages, gum, tea, vitamin complexes, functional food and the like. In addition, examples of the food include, but are not limited to, special nutrition food (for example, prepared milk, infant food and the like), processed meat products, fish products, tofu, jellied food (called "Muk"), noodles (for example, ramen, noodles, etc.), health improvement food, fermented seasoned food [for example, soy sauce, soybean paste (called "Doenjang"), red pepper paste (called "Gochujang"), mixed paste or the like)], sauces, confectionery (for example, snacks), processed milk products (for example, fermented milk, cheese and the like), other processed food, Kimchi, pickled (seasoned) food (for example, a variety of Kimchi, pickled vegetables and the like), beverages (for example, fruits, vegetable beverages, soy milk, fermented beverages, ice cream and the like), natural seasonings (for example, ramen soup base and the like), vitamin complexes, alcoholic beverages, liquors and other health supplement food. The functional food, beverages, food additives or beverage additives can be prepared by an ordinary preparation method.

As used herein, the term "functional food" refers to a group of food that has an added value imparted to enable the corresponding food to act and exhibit functions suited to certain purposes using a physical, biochemical, bio-engineering method or the like, or processed food, specifically, health functional food, that is designed to render a food composition to sufficiently exhibit the human body's regulation functions, such as regulation of the human body's defense rhythm, on the body, and disease prevention and recovery.

As used herein, the term "health functional food" refers to food that can be produced and processed into the form of a tablet, capsule, powder, granule, liquid or pill. As used herein, the term "function" means obtaining an effect useful for regulation of nutrients for human body structures and functions, or for sanitation such as physiological actions. The health functional food of the present invention can be produced by a method ordinarily used in the art, and the production is carried out by adding ingredients and materials ordinarily added in the art. In addition, any formulation of the health functional food can be prepared without limitation so long as it is considered to be applied to health functional food. The food composition of the present invention can be prepared into a variety of formulations, and has an advantage of being free of side-effects that may occur during long-term administration because it contains food as an ingredient, unlike general drugs. Due to excellent portability, the health functional food of the present invention can be administered as an adjuvant to improve the effects of inhibiting growth of breast cancer stem cells.

In addition, the functional food may contain a sitologically acceptable food auxiliary additive and may contain a suitable carrier, excipient and diluent ordinarily used in the production of functional food.

In addition, the amount of PAA in the food composition may be, based on the total weight of the food composition, 0.00001% by weight or more, specifically 0.1% by weight or more, and 80% by weight or less, specifically 50% by weight or less, more specifically 40% by weight or less. When the food is a beverage, it may be present, based on 100 ml of the total volume of food, in an amount of 0.001 g or more, specifically 0.01 g or more, 50 g or less, specifically 10 g or less, more specifically 2 g or less, but is not limited thereto.

The food composition of the present invention may further contain, in addition to the active ingredient, a sweetener, a flavoring agent, a physiologically active ingredient, a mineral or the like. The sweetener may be used in an amount to impart suitable sweet taste to food and may be natural or synthetic. Specifically, when the natural sweetener is used, examples of the natural sweetener may include sugar sweeteners such as solidified corn syrup, honey, sucrose, fructose, lactose and maltose. The flavoring agent may be used to improve taste or flavor and may be either natural or synthetic, specifically, natural. When the natural flavoring agent is used, strengthening of nutrients, apart from improvement of flavor may be achieved. For example, the natural flavoring agent may be derived from apple, lemon, citrus, grape, strawberry, peach and the like, or obtained from green tea leaves, Solomon's seal (dongle), bamboo leaves, cinnamon, chrysanthemum leaves, jasmine and the like. In addition, the natural flavoring agent may be obtained from ginseng (red ginseng), bamboo shoots, aloe vera, ginkgo and the like. The natural flavoring agent may be a liquid concentration or a solid extract. In some cases, a synthetic flavoring agent may be used. The synthetic flavoring agent may be ester, alcohol, aldehyde, terpene or the like. Examples of the biologically active substance include catechins such as catechin, epicatechin, gallocatechin and epigallocatechin, and vitamins such as retinol, ascorbic acid, tocopherol, calciferol, thiamine, riboflavin and the like. Examples of the mineral include calcium, magnesium, chromium, cobalt, copper, fluoride, germanium, iodine, iron, lithium, magnesium, manganese, molybdenum, phosphorus, potassium, selenium, silicon, sodium, sulfur, vanadium, zinc and the like.

In addition, the food composition of the present invention may include, in addition to the sweetener or the like, a preservative, an emulsifier, an acidulant, a thickener or the like.

The preservative, emulsifier or the like is preferably used in a minimal amount so long as the addition application thereof can be accomplished. The term "minimal amount" refers to the range from 0.0005% by weight to about 0.5% by weight, based on the total amount of the food composition. Useful preservatives include calcium sorbate, sodium sorbate, potassium sorbate, calcium benzoate, sodium benzoate, potassium benzoate, ethylene diamine tetraacetic acid (EDTA) or the like. Examples of useful emulsifiers include acacia gum, carboxymethyl cellulose, xanthan gum, pectin and the like. Examples of useful acidulants include citric acid, malic acid, fumaric acid, adipic acid, phosphoric acid, gluconic acid, tartaric acid, ascorbic acid, acetic acid, phosphoric acid and the like. The acidulant may be added such that the food composition has an appropriate acidity in order to improve taste as well as inhibit proliferation of microorganisms. Examples of useful thickeners include suspending agents, coagulants, gel formers, bulking agents and the like.

In another aspect, the present invention is directed to a pharmaceutical composition for inhibiting metastasis of breast cancer, or for treating or preventing breast cancer including the composition for inhibiting growth of breast cancer stem cells.

As used herein, the terms "cancer", "inhibition of growth of breast cancer stem cells", and "pharmaceutical composition" are as defined above.

As used herein, the term "metastasis" means the condition in which malignant tumors spread from organs where they occur to other separate tissues.

Figure 1A:
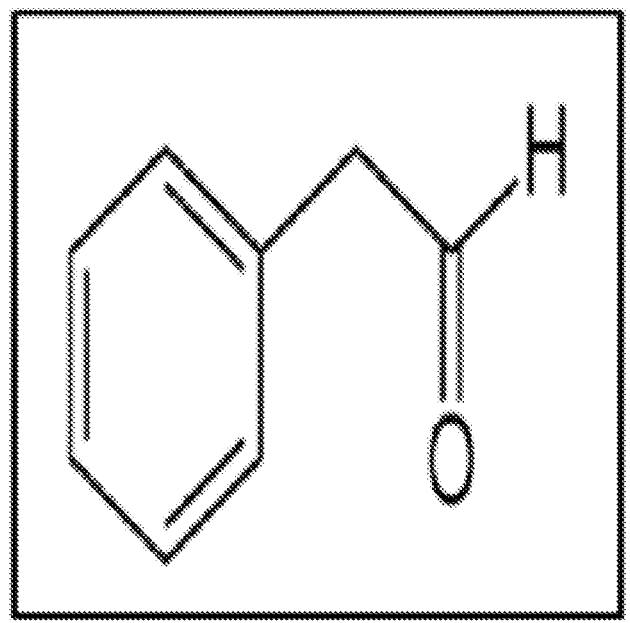
Figure 1B:
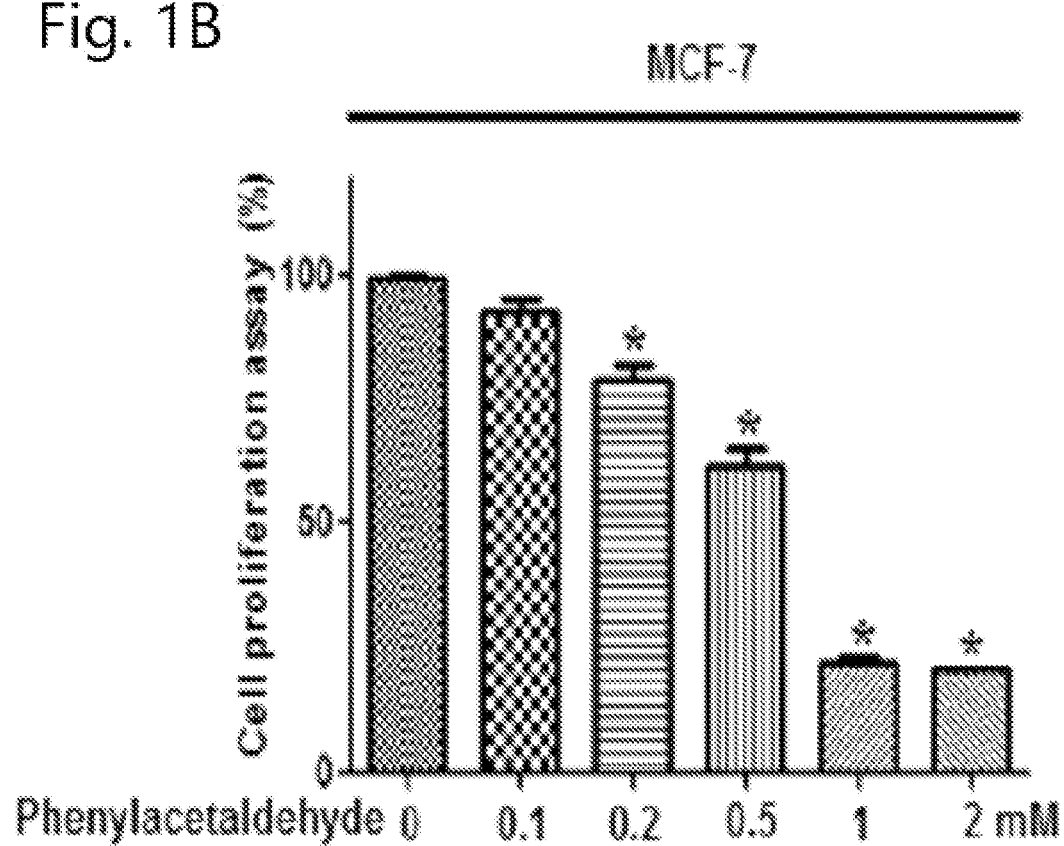
Figure 2A:
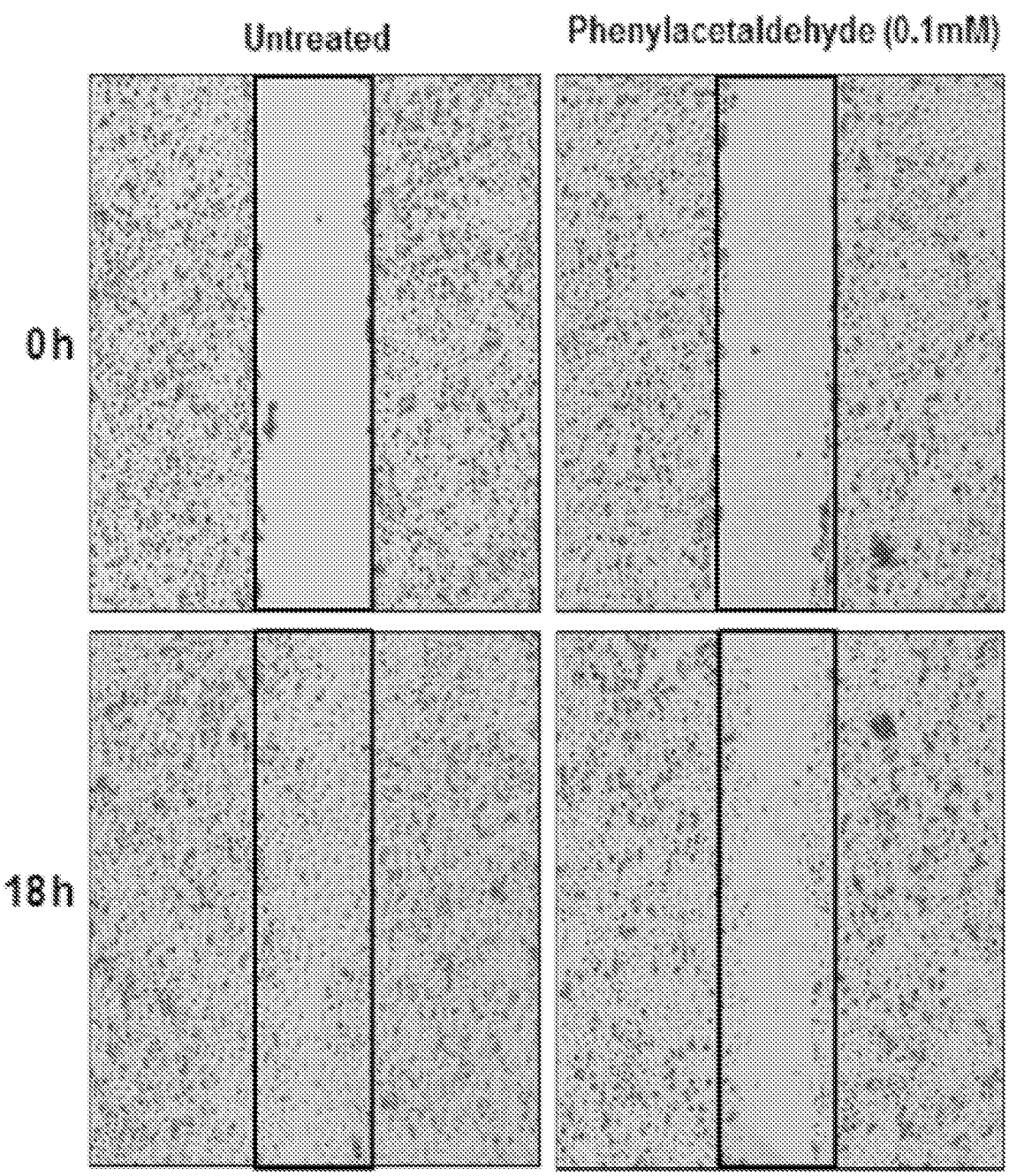
FIGS. 2A and 2B show that PAA inhibits a variety of cancer characteristics in breast cancer cell lines.
Figure 2B:
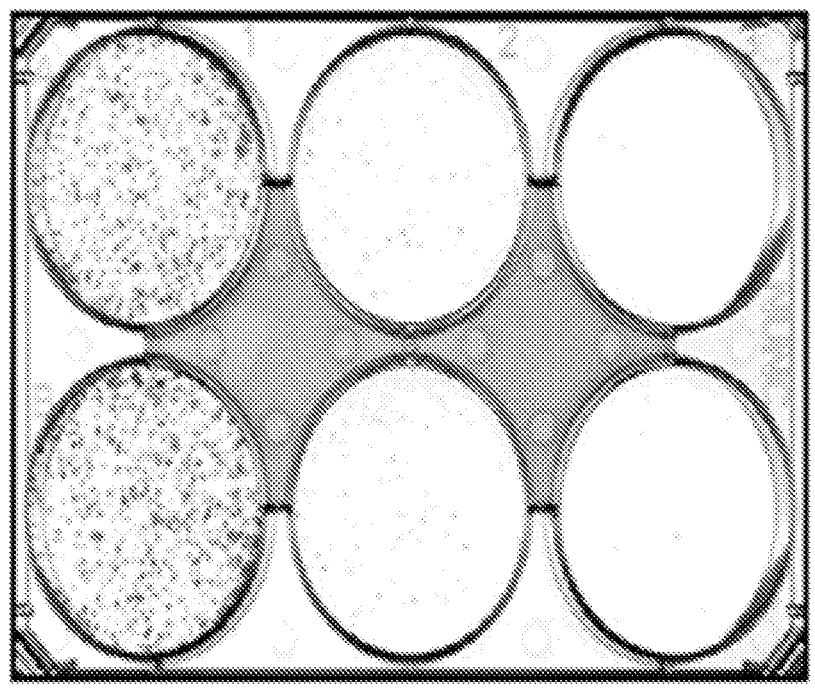

In one embodiment of the present invention, it is found that, growth of breast cancer cell lines is inhibited, when an MCF-7 cell line and an MDA-MB-231 cell line are treated with PAA (FIGS. 1B and 1C). Accordingly, the composition of the present invention may be used as a pharmaceutical composition for treating or preventing breast cancer. In addition, it is found that PAA concentration-dependently inhibits migration of MDA-MB-231 cells and formation of colonies (FIGS. 2A and 2B). Accordingly, the pharmaceutical composition containing PAA can be used as a pharmaceutical composition for treating or preventing breast cancer as well as for inhibiting metastasis of breast cancer.

Figure 6B:
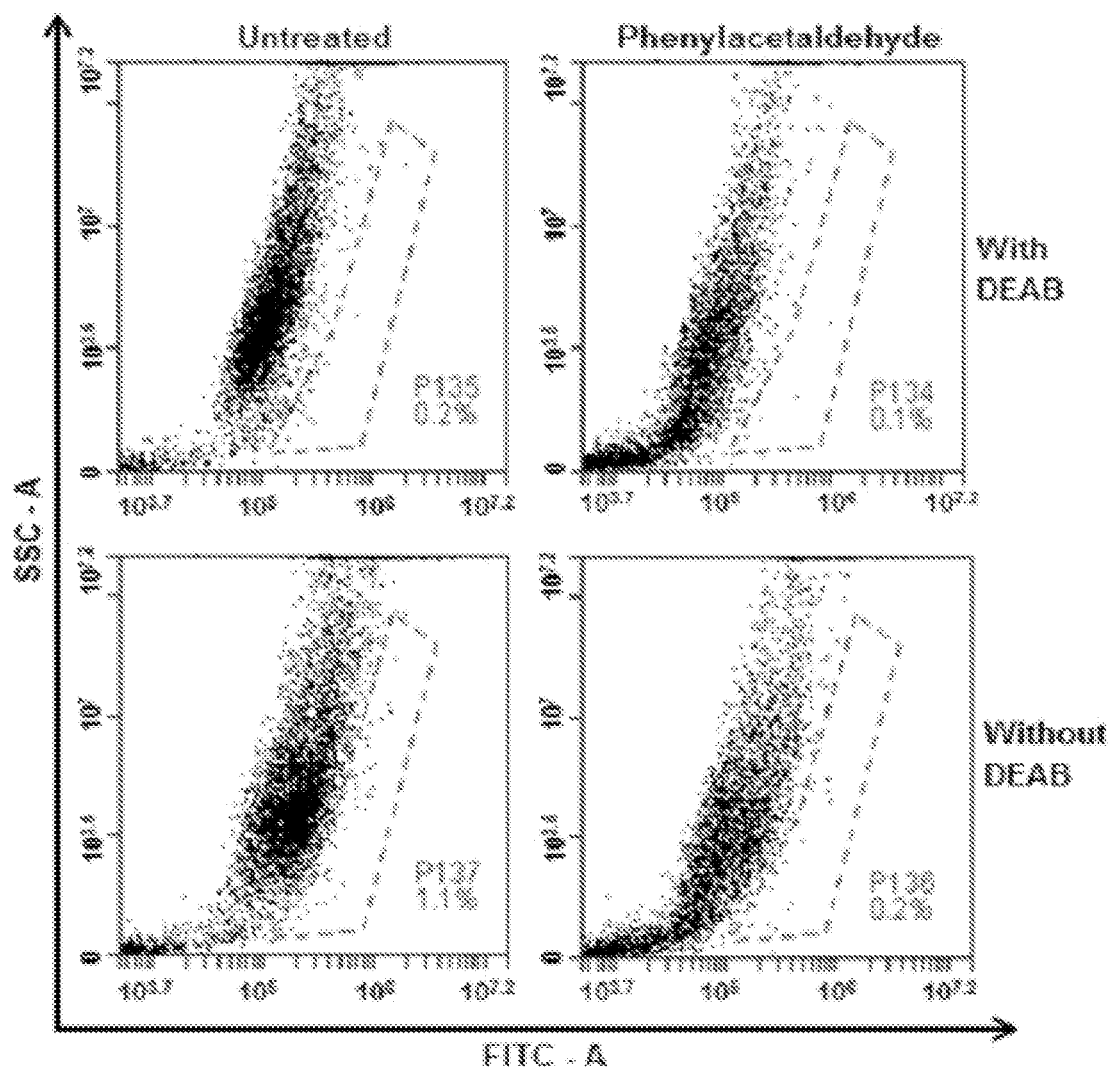

In one embodiment of the present invention, a PAA inhibitor reduces the population of breast cancer cells expressing $CD44^{high}/CD24^{low}$ (FIG. 6A), and reduces the proportion of ALDH positive breast cancer cells to a level of 0.9% to 0.1% (FIG. 6B). Accordingly, the composition of the present invention can inhibit growth of breast cancer cells expressing $CD44^{high}/CD24^{low}$, and inhibit growth of aldehyde dehydrogenase (ALDH)-positive breast cancer cells.

In another aspect, the present invention provides a food composition for inhibiting metastasis of breast cancer, or for alleviating or preventing breast cancer including the composition for inhibiting growth of breast cancer stem cells.

As used herein, the terms "cancer", "inhibition of growth of breast cancer stem cells", "metastasis", and "food composition" are as defined above.

In another aspect, the present invention provides a perfume composition for inhibiting growth of breast cancer stem cells containing the following volatile compound represented by Formula 1:

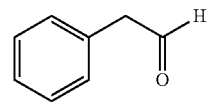

[Formula 1]

As used herein, the terms "compound represented by Formula 1", "cancer", "breast cancer stem cells", and "inhibition of growth of breast cancer stem cells" are as defined above.

The compound of the present invention is phenylacetaldehyde (PAA). In addition, the composition of the present invention may further include at least one compound selected from phenylethanol, 2-phenylpropionaldehyde, and 3-phenylpropionaldehyde.

As used herein, the term "volatility" means the property in which an ingredient of a substance, which has a low boiling point in a liquid or solid state at room temperature, evaporates or sublimes. When the steam pressure of a substance increases, volatility further increases. A liquid fuel, gasoline, an organic solvent and an aromatic compound including benzene having a low boiling point have high volatility due to detachment of molecules from the surface of a liquid or solid.

As used herein, the term "perfume" means a substance emitting fragrance. When the perfume enters the nose together with inspired air and reaches the nostril, it can stimulate the olfactory system to provide pleasure and is classified into natural perfumes including essential oils extracted from animals and plants, and synthetic perfumes. The synthetic perfumes include those having the same structures as natural perfumes and those having a similar fragrance to natural perfumes synthesized from or combined with other ingredients. In addition, they are organic substances having strong fragrance added in order to impart fragrance to daily supplies such as cosmetics and food products, which exhibit excellent volatility at room temperature.

Figure 4C:
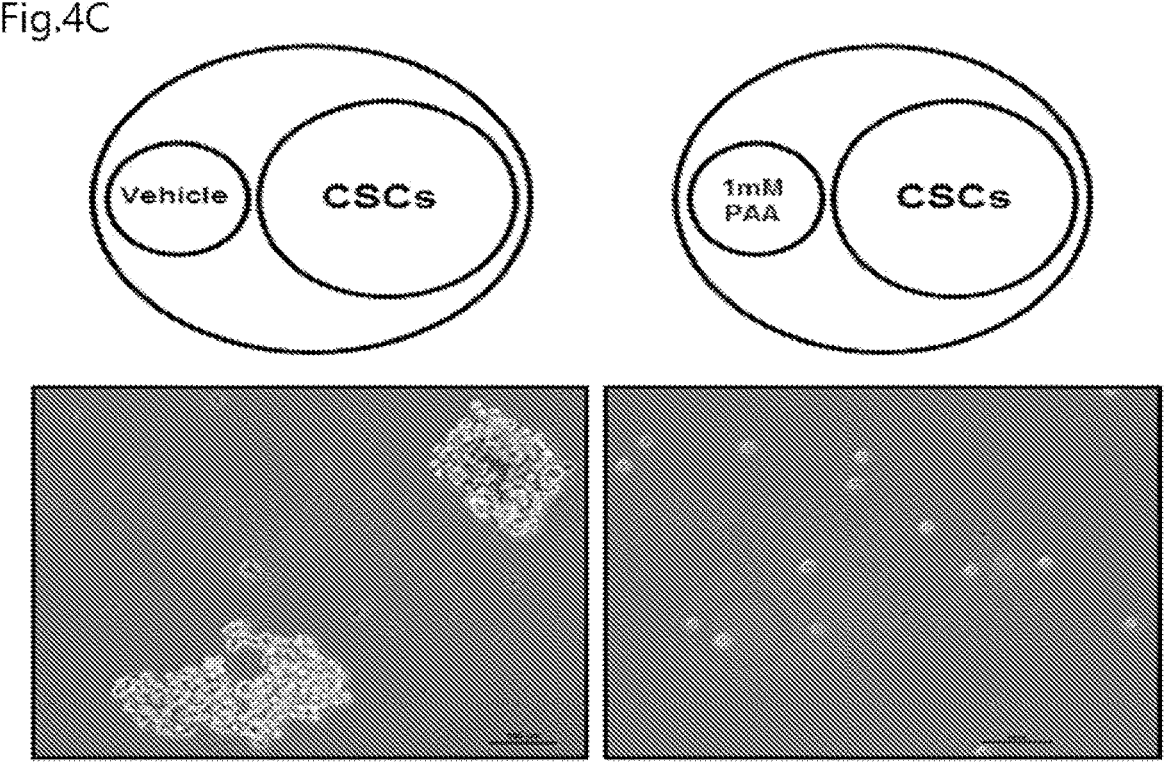

In one embodiment of the present invention, it was analyzed whether or not formation of breast cancer stem cells (CSCs) can be inhibited by emission of fragrance from the PAA compound (FIG. 4C). As a result, it could be seen that PAA inhibits formation of mammospheres to suppress formation of CSCs, and PAA, which is the most important volatile material for roses and tomatoes, as well as, phenylethanol, which is a phenylalanine-derived volatile material, 2-phenylpropionaldehyde and 3-phenylpropionaldehyde, inhibit formation of breast cancer stem cells.

Accordingly, the volatile compound represented by Formula 1 according to the present invention can inhibit growth of breast cancer stem cells through fragrance emitted from the volatile compound and can be used as a perfume composition capable of inhibiting growth of breast cancer stem cells.

In another aspect, the present invention provides a pharmaceutical composition including the perfume composition.

According to the present invention, the PAA can inhibit growth of breast cancer stem cells through fragrance emitted from the volatile compound and can be used as a perfume composition capable of inhibiting growth of breast cancer stem cells.

As used herein, the term "pharmaceutical composition" is as defined above.

In another aspect, the present invention provides a skin preparation for external use containing the perfume composition.

According to the present invention, the PAA is the volatile compound and thus can inhibit growth of breast cancer stem cells through fragrance emitted therefrom and can be used as a skin preparation for external use. Examples of the skin preparation for external use according to the present invention include ointments, lotions, suspensions, emulsions, creams, gels, sprays, cataplasms, plasters, patches or liquid-type patches, but are not limited thereto. The skin preparation for external use may be mixed with any base material well-known in the art. The skin preparation for external use according to the present invention may be present in an amount of 0.01 to 20% by weight, with respect to the total weight of the perfume composition.

In another aspect, the present invention provides a food composition including the perfume composition.

The perfume composition of the present invention may be used as a food composition and the term "food composition" is as defined above.

In another aspect, the present invention provides a cosmetic composition including the perfume composition.

The cosmetic composition of the present invention may contain other ingredients added to the cosmetic composition well-known in the art, apart from the aforementioned perfume composition. The cosmetic composition of the present invention is basically applied to the skin, may be provided with reference to the cosmetic composition known in the art and may be, for example, formulated into a solution, suspension, emulsion, paste, gel, cream, lotion, powder, soap, surfactant-containing cleansing agent, oil, powdery foundation, emulsion foundation, wax foundation, spray or the like, but is not limited thereto. More specifically, the cosmetic composition may be prepared into a formulation such as softening skin lotion, nutritional skin lotion, nutritional cream, massage cream, essence, eye cream, cleaning cream, cleaning form, cleaning water, pack, spray or powder.

When the formulation of the present invention is a paste, cream or gel, an animal oil, a vegetable oil, a wax, paraffin, starch, tragacanth, a cellulose derivative, polyethylene glycol, silicon, bentonite, silica, talc or zinc oxide may be used as the carrier ingredient.

When the formulation of the present invention is a powder or spray, lactose, talc, silica, aluminum hydroxide, calcium silicate or polyamide powder may be used as the carrier ingredient. In particular, when the formulation is a spray, it may include a propellant such as chlorofluorohydrocarbon, propane/butane or dimethyl ether.

When the formulation of the present invention is a solution or an emulsion, a solvent, solubilizing agent or emulsifying agent is used as the carrier ingredient, and examples thereof include water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan.

When the formulation of the present invention is a suspension, as the carrier ingredient, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, tragacanth or the like may be used.

When the formulation of the present invention is a surfactant-containing cleansing agent, as the carrier ingredient, aliphatic alcohol sulfate, aliphatic alcohol ether sulfate, monoester sulfosuccinate, isethionate, imidazolinium derivatives, methyltaurate, sarcosinate, fatty acid amide ether sulfate, alkyl amido betaine, aliphatic alcohol, fatty acid glyceride, fatty acid diethanolamide, vegetable oil, lanolin derivatives, ethoxylated glycerol fatty acid ester or the like may be used.

In another aspect, the present invention provides a personal care product containing the perfume composition.

The perfume composition of the present invention may be mixed with a hair product such as shampoo, conditioner, treatment, hair essence; an oral product such as toothpaste or mouthwash; a skin cleanser such as body wash, body gel and soap not so as to impair the objects of the present invention, so that it can be provided in the form of a personal care product.

In another aspect, the present invention provides a home care product containing the perfume composition.

The perfume composition of the present invention may be mixed with an air freshener such as perfume, a detergent such as kitchen detergent or a laundry detergent not so as to impair the objects of the present invention, so that it can be provided in the form of a home care product. In this case, in order to improve physical properties of the composition, a fragrance, pigment, bactericide, antioxidant, preservative, moisturizer, thickener, inorganic salt, synthetic polymer or the like may be further added.

In another aspect, the present invention provides an air freshener composition including the perfume composition. That is, the perfume composition of the present invention may be added to the air freshener composition.

The air freshener composition of the present invention may contain 0.001 to 30% by weight, preferably 1 to 30% by weight, more preferably 1 to 10% by weight of the perfume composition, based on the total weight of the composition. When the perfume composition is present in an amount less than 0.001% by weight of the total composition, smelling is difficult due to poor scent emission, and when the perfume composition is added in an amount higher than 30% by weight, the scent is too strong to be used as an air freshener.

When the perfume composition of the present invention is used as an air freshener additive, the composition may be added in itself or may be used in combination with any ingredient useful for a flavoring agent or an air freshener composition. In particular, these may be mixed with a wide range of one or more of natural, synthetic and synthetic chemical substances, natural air fresheners, flavoring agent materials, and natural extracts used in flavoring agents or air fresheners. In addition, the air freshener composition may contain one or more ingredients or excipients, commonly used in combination with a flavoring agent and an air freshener, for example, carrier materials, thickeners, flavor enhancers and other adjuvants commonly well-known in the art. The air freshener composition of the present invention may provide a gel or solidified composition for volatile-type air freshener application, or a liquid composition for spray-type air freshener application.

In another aspect, the present invention provides an additive for humidifiers containing the perfume composition.

The perfume composition of the present invention has volatility so that it can be used as an active ingredient for the humidifier additive.

In another aspect, the present invention provides a cigarette filter containing the perfume composition.

The perfume composition of the present invention has volatility, so that it can be used for the production of the cigarette filter.

In another aspect, the present invention provides an electronic cigarette containing the perfume composition.

The perfume composition of the present invention has volatility, so that it can be used for the production of electronic cigarettes. The perfume composition of the present invention may be applied to an atomizer or electronic cigarette to be vaporizable or may be produced into fine particles to be inhalable. The electronic cigarette or atomizer means an electronic device that converts a fragrant or inhalable ingredient added to a solvent such as propylene glycol, vegetable glycerin or water into a gas or fine particle. Gasification (conversion into a gas) means that a liquid ingredient changes into a gas ingredient, for example, due to Joule resistance heat resulting from power supply. In addition, conversion into a fine particle means that a liquid is atomized by a nozzle structure or ultrasonication. The electronic cigarette is designed to inhale the perfume composition by a gasification method and the atomizer is designed to produce an inhalable particle using a nozzle structure or ultrasonication. In addition, the perfume composition can be produced into an inhalable form by a variety of methods.

In another aspect, the present invention provides a method for inhibiting growth of breast cancer stem cells including exposing the following volatile compound represented by Formula 1 to breast cancer stem cells in a subject:

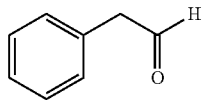

[Formula 1]

As used herein, the terms "compound represented by Formula 1", "volatility", "cancer", "breast cancer stem cells", and "inhibition of growth of breast cancer stem cells" are as defined above.

As used herein, the term "subject" refers to any animal including human with the onset or metastasis of breast cancer and includes mammals including cows, pigs, sheep, chickens, dogs and human, birds and the like. Any subject may be used without limitation so long as growth of breast cancer stem cells thereof is inhibited through the volatile compound of the present invention and cancer thereof is treated by the compound.

The volatile compound represented by Formula 1 according to the present invention has volatility so that, when the compound is exposed to breast cancer stem cells, growth of the breast cancer stem cells can be inhibited by emission of fragrance from the compound.

In another aspect, the present invention provides a method for inhibiting growth of breast cancer stem cells including administering the following compound represented by Formula 1 or a pharmaceutically acceptable salt thereof to a subject:

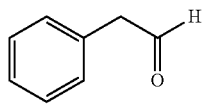

[Formula 1]

As used herein, the terms "compound represented by Formula 1", "subject, "cancer", "breast cancer stem cells", and "inhibition of growth of breast cancer stem cells" are as defined above.

The compound of the present invention represented by Formula 1 inhibits growth of breast cancer stem cells. Accordingly, growth of the breast cancer stem cells is inhibited by administration of the compound.

In another aspect, the present invention provides a method for inhibiting metastasis of breast cancer including administering the following compound represented by Formula 1 or a pharmaceutically acceptable salt thereof to a subject:

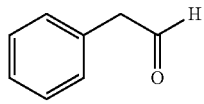

[Formula 1]

As used herein, the terms "compound represented by Formula 1", "cancer", "subject", and "metastasis of breast cancer" are as defined above.

In another aspect, the present invention provides a method for treating or preventing breast cancer including administering the following compound represented by Formula 1 or a pharmaceutically acceptable salt thereof to a subject:

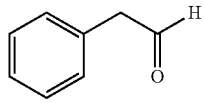

[Formula 1]

As used herein, the terms "compound represented by Formula 1", "cancer", "subject", "treatment of breast cancer", and "prevention of breast cancer" are as defined above.

In another aspect, the present invention provides use of the following compound represented by Formula 1 or a pharmaceutically acceptable salt thereof for the production of a drug for inhibiting growth of breast cancer stem cells:

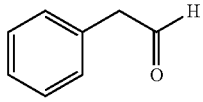

[Formula 1]

As used herein, the terms "compound represented by Formula 1", "cancer", "breast cancer stem cells", and "inhibition of growth of breast cancer stem cells" are as defined above.

In another aspect, the present invention provides use of the following compound represented by Formula 1 or a pharmaceutically acceptable salt thereof for the production of a drug for inhibiting metastasis of breast cancer:

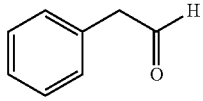

[Formula 1]

As used herein, the terms "the compound represented by Formula 1", "cancer" and "breast cancer metastasis" are as defined above.

In another aspect, the present invention provides use of the following compound represented by Formula 1 or a pharmaceutically acceptable salt thereof for the production of a drug for preventing or treating breast cancer:

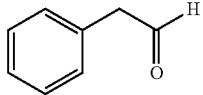

[Formula 1]

As used herein, the terms "compound represented by Formula 1", "cancer", "treatment of breast cancer" and "prevention of breast cancer" are as defined above.

MODE FOR INVENTION

Hereinafter, the present invention is described with reference to examples in more detail. The examples are provided only for illustration of the present invention and should not be construed as limiting the scope of the present invention.

A: TEST MATERIAL AND METHOD

Example 1: Test Material 6- and 24-well culture plates including very low-attachment cluster plates were commercially available from Corning (Tewksbury, Mass., USA). A perfume compound containing phenylacetaldehyde was purchased from Sigma-Aldrich Co. (St. Louis, Mo., USA). Cell viability was measured using a CellTiter 96® aqueous one solution cell proliferation assay kit (Promega, Madison, Wis., USA). An ALDEFLUOR™ Kit was purchased from STEMCELL Technologies Inc (Vancouver, BC, Canada). For example, a chemical reagent such as doxorubicin was purchased from Sigma-Aldrich Co. (St. Louis, Mo., USA).

Example 2: Culture of Human Breast Cancer Cells and Formation of Mammospheres

Human breast cancer cells, i.e., MCF-7 and MDA-MB-231, were commercially obtained from American Type Culture Collection (ATCC; Manassas, Va., USA). MCF-7 and MDA-MB-231 cells were cultured in Dulbecco's modified essential medium (DMEM; Hyclone, Logan, Utah, USA) containing 10% fetal bovine serum (FBS; Hyclone), 100 U/mL of penicillin, and 100 µg/mL of streptomycin (Hyclone). The MCF-7 and MDA-MB-231 cells were maintained at 37° C. in a 5% $CO_2$-containing humidified incubator. The cells were plated at a density of $1\times10^6$ on a 10 cm petri dish. In order to establish primary mammospheres, single cell-suspended MCF-7 and MDA-MB-231 cells were seeded at a density (cells/well) of $3.5\times10^4$ to $4\times10^4$ and $0.5\times10^4$ to $1\times10^4$, respectively, on ultra-low attachment 6-well plates containing 2 ml complete MammoCult™ medium (StemCell Technologies, Vancouver, BC, Canada). The complete MammoCult™ medium was supplemented with 4 µg/mL of heparin, 0.48 µg/mL of hydrocortisone, 100 U/mL of penicillin and 100 µg/mL of streptomycin. The cells were cultured for 7 days in a 37° C. 5% $CO_2$ incubator.

Example 3: Automatic Calculation of Mammospheres

At 7 days of culture, the cell culture plate was disposed on a scanner (Epson Perfection V700 PHOTO, Epson Korea, Co, Seoul, Korea) to obtain an 8 bit gray scale image of mammospheres. The image was obtained at a low resolution (300 dpi) using an NICE software program and downloaded from ftp://ftp.nist.gov/pub/physics/mLclarke/NICE. For counting, preferred numbers of rows and columns (for example, 2×3 of 6-well plate) were selected to form regions of interest (ROIs), and an oval setting of the NICE program was selected and then respective ROIs were defined by moving the shapes of provided ROIs and controlling the sizes thereof. The background signal of the image was negated using a critical algorithm and the selected image was automatically counted. Regarding the mammosphere formation analysis, formation efficiency of mammospheres (MFE, %) was determined in accordance with the number of mammospheres per well/the total number of cells plated per well×100.

Example 4: Cell Proliferation Analysis

Proliferation rates of MCF-7 and MDA-MB-231 cells were measured using a CellTiter 96® aqueous one solution cell proliferation kit. MCF-7 and MDA-MB-231 cells were cultured in the presence of PAA (0.1, 0.2, 0.5, 1 and 2 mM) on a 96-well plate for 48 hours. In accordance with the manufacturer's protocol, absorbance at 490 nm was determined using a 96-well plate reader (Dynex Revelation, Dynex Ltd., Billingshurst, UK). All data was determined by measurement of three sets.

Example 5: Caspase-3/7 Analysis

Cancer cells were treated with different concentrations of PAA for 24 hours. Caspase-3/7 activity was analyzed in accordance with the manufacturer's instructions regarding a Caspase-Glo 3/7 kit (Promega, Wis., USA). 100 μl of a Caspase-Glo 3/7 reagent was added to a 96-well for culturing cancer cells. The plate was covered with a plate sealer and cultured at room temperature for one hour, and Caspase-3/7 activity was measured using a plate-reading luminometer, GloMax® Explorer (Promega, Wis., USA).

Example 6: Annexin V/PI Staining Analysis

Cancer cells were cultured on a 6-well plate and incubated together with PAA (0.5 mM) or DMSO for 24 hours. In accordance with the manufacturer's instructions, the cancer cells were double-stained with PI and FITC-Annexin V. The sample was analyzed by flow cytometry (Accuri C6, BD, San Diego, Calif., USA).

Example 7: Analysis of Apoptosis by Fluorescent Staining

MDA-MB-231 cells were treated with 200 μm of PAA for 24 hours and were cultured in a Hoechst 33258 solution (10 mg/mL) at 37° C. for 30 minutes. Then, the cells were observed with a fluorescent microscope.

Example 8: Clonogenicity Assay

MDA-MB-231 cells were seeded at a low density on a 6-well plate and treated with different concentrations of PAA in DMEM. After 24 hours, the medium was replaced with fresh medium and incubated for cell growth for 7 days. Grown colonies were counted.

Example 9: Scratch Migration Assay

MDA-MB-231 cells were seeded on a 6-well plate to grow cells until confluence reached 90%. Scratch was created on the cell layer using a sterilized white micro-pipette tip. After washing with DMEM medium, breast cancer cells were treated with PAA or DMSO. 16 hours later, the scratch region was imaged with a 10× optical microscope.

Example 10: Flow Cytometric Analysis of CD44 and CD24 Expression

Expression of CD44 and CD24 in MDA-MB-231 cells was measured by FACS analysis. The cells were isolated and harvested using 1× trypsin/EDTA, and a million of cells were suspended, labelled with FITC-conjugated anti-human CD44 and PE-conjugated anti-human CD24 antibodies (BD Pharmingen, San Diego, Calif., USA) and cultured at 4° C. for 30 minutes. Then, the cells were washed with 1×PBS three times and analyzed by flow cytometry (Accuri C6, BD, San Diego, Calif., USA).

Example 11: Measurement of ROS Activity

Cancer cells were cultured on a 96-well white plate and cultured together with PAA (0.5 mM) or DMSO for 24 hours. In accordance with the manufacturer's instructions, ROS was measured using an ROS-Glo™ $H_2O_2$ detection solution (Promega, Wis., USA). 100 μl of the ROS-Glo™ $H_2O_2$ detection solution was added to a 96-well white plate containing breast cancer cells, cultured at room temperature for 20 minutes, and relative luminance was recorded using a plate reader, luminometer, GloMax® Explorer (Promega, Wis., USA).

Example 12: Real-Time PCR (RT-PCR)

In accordance with the manufacturer's instructions, the level of transcriptome was measured with one step SYBR PrimeScript RT-PCR kit (Takara, Tokyo, Japan) using SYBR green as a double-stranded DNA-specific dye. One-step RT-PCR reaction was conducted in the final volume of 20 μl per reaction containing 1 μg of total RNA, 10 μl of 2× one step SYBR RT-PCR buffer IV, 1 μl of PrimeScript 1 step enzyme mix II, and 10 μM of PCR forward primers and PCR reverse primers for CD44, NANOG, OCT4, SOX2, and β-actin. The forward and reverse primers are as follow:

```
CD44 forward primer:
                                           (SEQ NO. 1)
AGAAGGTGTGGGCAGAAGAA, CD44 reverse primer:
                                           (SEQ NO. 2)
AAATGCACCATTTCCTGAGA, NANOG forward primer:
                                           (SEQ NO. 3)
ATGCCTCACACGGAGACTGT, NANOG reverse primer:
                                           (SEQ NO. 4)
AAGTGGGTTGTTTGCCTTTG, OCT4 forward primer:
                                           (SEQ NO. 5)
AGCAAAACCCGGAGGAGT, OCT4 reverse primer:
                                           (SEQ NO. 6)
CCACATCGGCCTGTGTATATC, SOX2 forward primer:
                                           (SEQ NO. 7)
TTGCTGCCTCTTTAAGACTAGGA, SOX2 reverse primer:
                                           (SEQ NO. 8)
CTGGGGCTCAAACTTCTCTC, β-actin forward primer:
                                           (SEQ NO. 9)
TGTTACCAACTGGGACGACA, β-actin reverse primer:
                                           (SEQ NO. 10)
GGGGTGTTGAAGGTCTCAAA.
```

Relative expression amounts of mRNAs of target genes were calculated using a comparative CT method. At least three independent PCR procedures were conducted in accordance with statistical analysis. PCR products were normalized with β-actin genes, as an internal control.

Example 13: ALDEFLUOR Assay

An ALDEFLUOR assay system provides a novel approach regarding identification, evaluation and separation of CSCs based on activity of aldehyde dehydrogenase (ALDH). BODIPY-aminoacetaldehyde was added as an active reagent to breast cancer cells and converted into fluorescent BODIPY-aminoacetate by aldehyde dehydrogenase (ALDH). An ALDH inhibitor, i.e., diethylaminobenzaldehyde (DEAB), was used as a negative control group.

MCF-7 cells were treated with 200 μM of PAA for 24 hours, and the rate of ALDH-positive cells was analyzed by ALDE-FLUOR assay. ALDH positive and negative cells were classified by flow cytometry (Accuri C6, BD, San Diego, Calif., USA).

Example 14: Western Blotting

The proteins isolated from mammospheres of PAA-treated MCF-7 were separated on 10% SDS-PAGE and transferred to a polyvinylidene difluoride membrane (Millipore, Bedford, Mass., USA). The membrane was blocked in 5% skim milk-containing PBS-Tween 20 (0.1%, v/v) for 30 minutes at room temperature. The blot was cultured at 4° C. in a blocking solution containing primary antibodies overnight. The used primary antibodies were as follows: Stat3, p65, Lamin B, and phospho-Stat3 (Cell Signaling, Beverly, Mass., USA). β-actin antibodies (Santa Cruz Biotechnology) were used as a loading control group. After washing with PBS-Tween 20 (0.1%, v/v), the blot was cultured in a horseradish peroxidase-conjugated secondary antibody and subjected to photosensitive treatment with a chemiluminescent detection kit (Santa Cruz Biotechnology).

Example 15: Electrophoretic Mobility Shift Assays (EMSAs)

In accordance with the manufacturer's instructions, EMSAs were detected using a chemiluminescent EMSA kit (Thermoscientific, IL, USA) commercially available from Lightshift. Biotin-top and bottom probe parts (5'-CTTCAT-TTCCCGGAAATCCCTA-Biotin3', SEQ NO. 11 and 5'-TAGGGATTTCCGGGAAATGAAG-Biotin3', SEQ NO. 12) of Stat3 probe were annealed and the double-stranded oligonucleotide was end-labelled with biotin. Nuclear extracts from MCF-7 and MDA-MB-231 cells were produced as suggested in the following Reference Document (Choi H S, Hwang C K, Kim C S, Song K Y, Law P Y, Wei L N and Loh H H. Transcriptional regulation of mouse mu opioid receptor gene: Sp3 isoforms (M1, M2) function as repressors in neuronal cells to regulate the mu opioid receptor gene. Mol Pharmacol. 2005; 67(5):1674-1683).

Biotin-labelled DNA probes were cultured together with PAA-treated nuclear proteins in a total volume of 20 μl of EMSA buffer containing 1 μg/μl poly[dI-dC]) for 20 minutes at room temperature. The reaction mixture was subjected to electrophoresis on 4% polyacrylamide nondenaturing gel at 4° C. in the presence of 0.5×TBE (45 mM Tris borate and 1 mM EDTA) and visualized using a chemiluminescence nucleic acid detection kit (Thermoscientific, IL, USA).

Example 16: Chemotherapy of Immunodeficient NOD-SCID (BALB/cSIc (nu/nu)) Female Nude Mice Producing Breast Cancer Cells 24 NOD-SCID (BALB/cSIc (nu/nu)) female nude mice in total were divided into four groups producing breast cancer cells. Six mice as a negative control group were not subjected to chemotherapy. However, the volumes of tumors of control group mice were measured every three days using the Equation of (width$^2$×length)/2 (FIG. 3). PAA was administered at the optimal dose of 10 to 50 mg/kg to six other nude mice via breast fat pad injection. In addition, doxorubicin (Dox) was administered daily in a low dose of 10 mg/kg to other six nude mice as a positive control group via breast fat pad injection. The last group was used as a non-tumor group without treatment.

Example 17: Statistical Analysis

All data is represented by mean±standard deviation (SD). Data was analyzed using a student's t-test. P<0.05 was considered to be statically significant (GraphPad Prism 5 Software, San Diego, Calif., USA).

B: TEST EXAMPLE

Test Example 1: Phenylacetaldehyde (PAA) Induces Apoptosis of Human Breast Cancer Cells and Inhibits Proliferation FIG. 1A shows chemical formula of the phenylacetaldehyde (PAA) according to the present invention. In order to investigate anti-proliferation effects of PAA in human breast cancer cell lines, i.e., MCF-7 and MDA-MB-231, the cancer cell lines were treated with different concentrations of PAA and then MTS analysis was conducted. As a result, 48 hours after PAA treatment, for the MCF-7 cell line, growth of breast cancer cell lines was concentration-dependently inhibited at a PAA concentration of 200 μm or more and, for the MDA-MB-231 cell line, growth of breast cancer cell lines was concentration-dependently inhibited at a PAA concentration of 100 μm or more (FIGS. 1B and 1C).

Figure 1D:
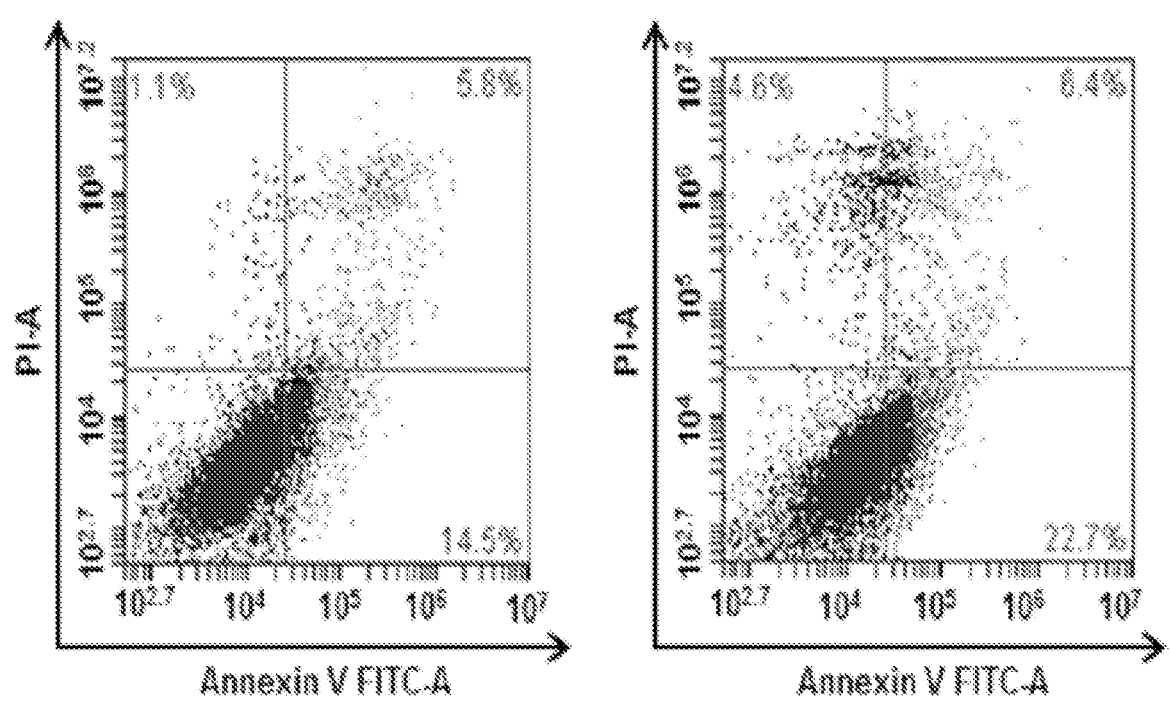
Figure 1E:
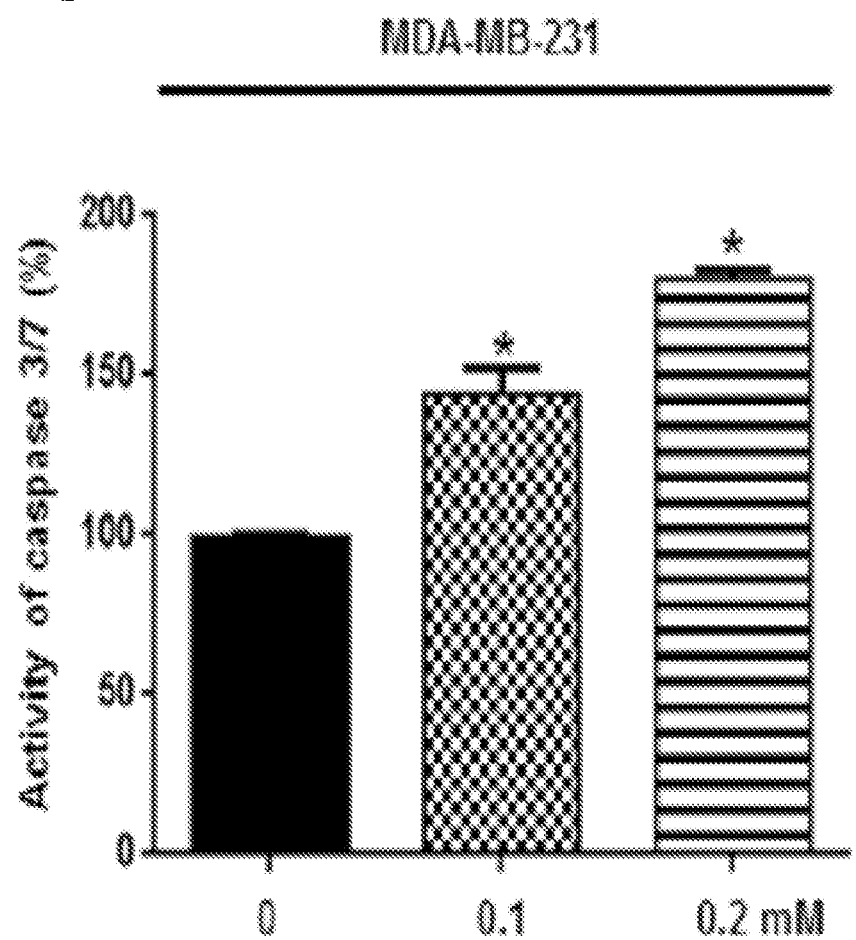
Figure 1F:
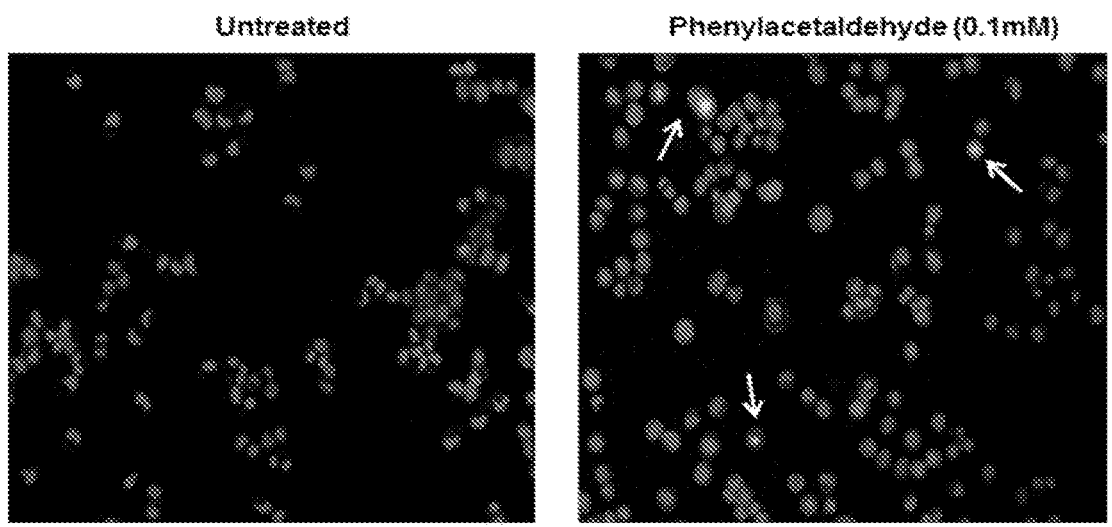

The number of breast cancer cells (Annexin V+) killed in MDA-MB-231 was increased by treatment with PAA 0.2 mM (FIG. 1D). Fluorescent analysis of caspase 3/7 was conducted in MDA-MB-231 to identify that PAA concentration-dependently induced activity of caspase 3/7 (FIG. 1E). After treatment with PAA, apoptotic bodies were formed in MDA-MB-231 breast cancer cells (FIG. 1F). In addition, PAA concentration-dependently inhibited migration of MDA-MB-231 cells and formation of colonies (FIGS. 2A and 2B). These results mean that PAA effectively inhibits a variety of cancer characteristics (proliferation, migration, apoptosis and colony formation).

Test Example 2: PAA Inhibits Tumor Growth in Xenograft Tumor Model

Figure 2B:
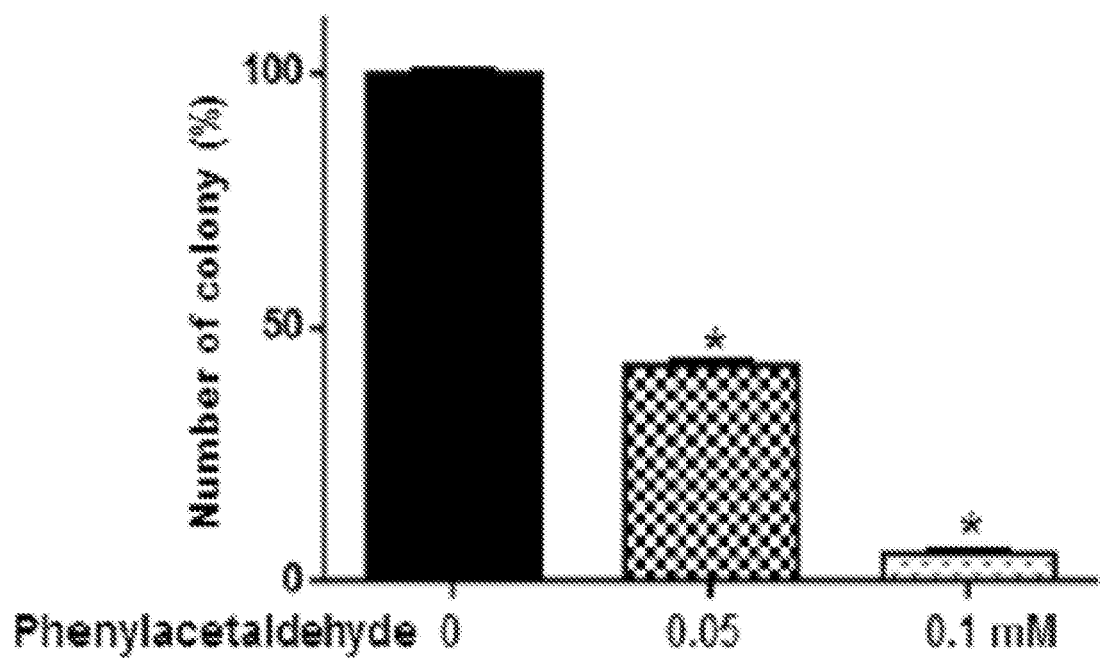
Figure 3A:
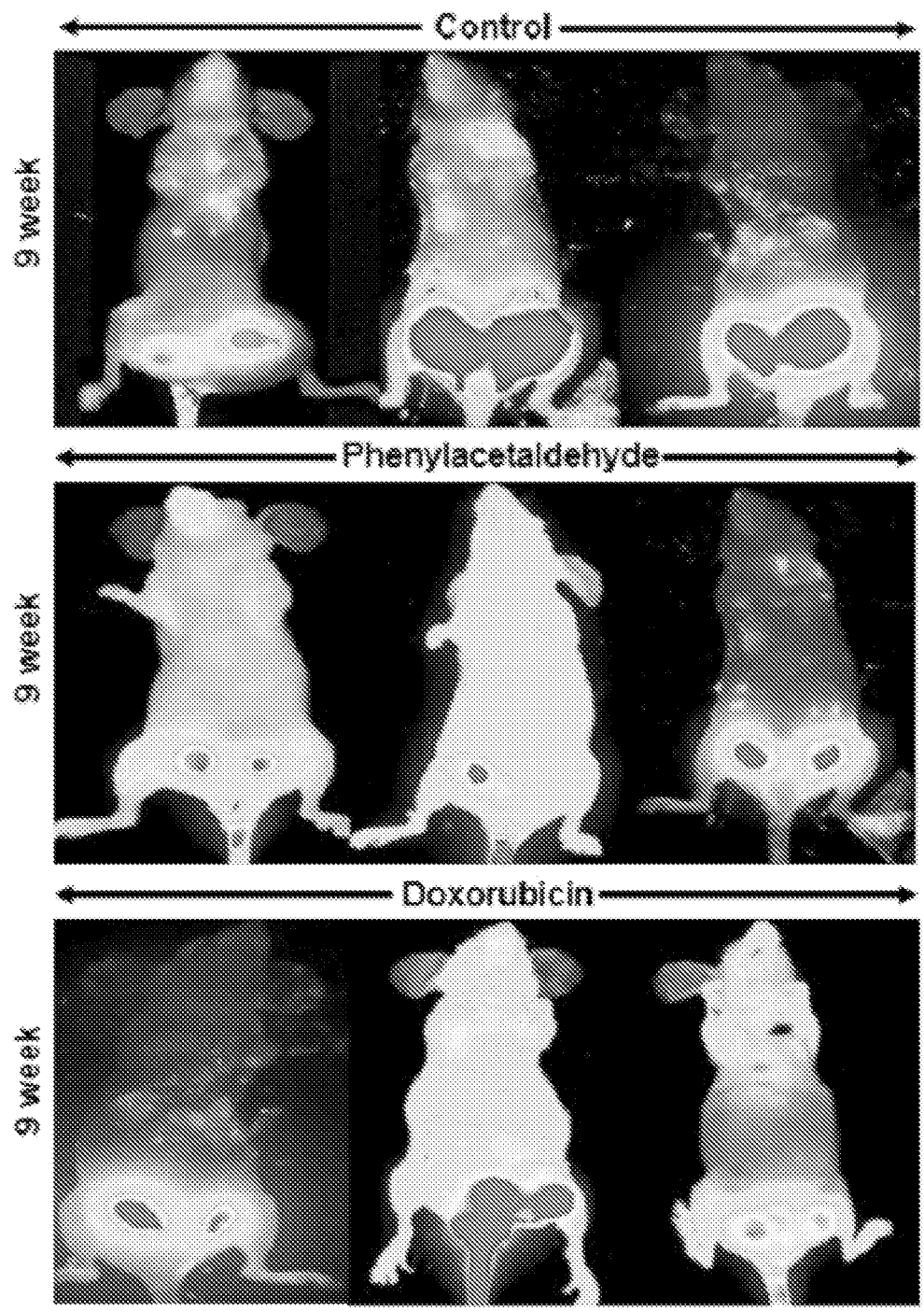
Figure 3B:
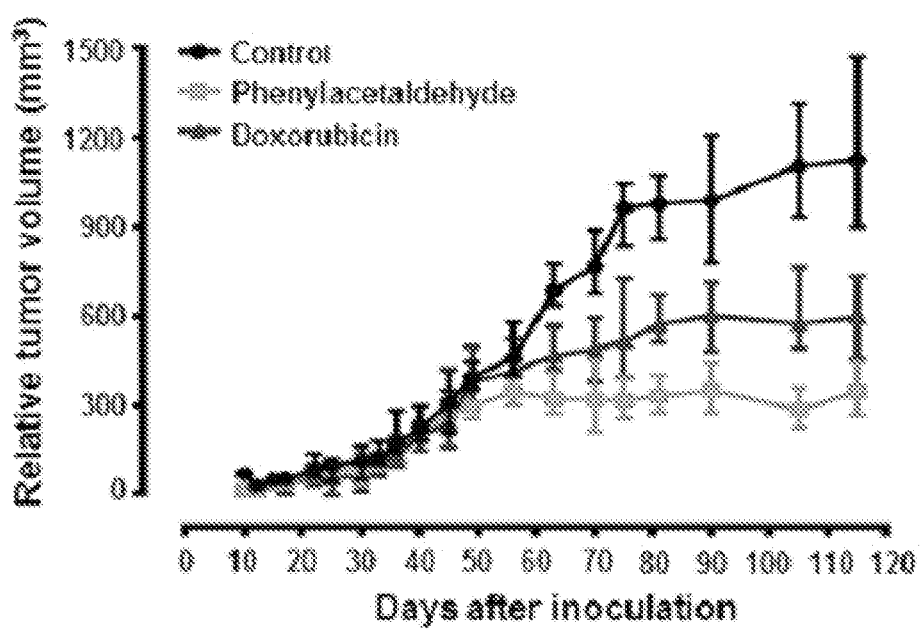

As can be seen from FIGS. 1 and 2, PAA inhibits proliferation of breast cancer cells in vitro. Then, it was investigated whether or not PAA inhibits induction of tumor in a xenograft tumor model. Tumor volume in the PAA treatment group was less than that of a control group not treated with PAA, and was less than that of Doxorubicin as positive control group (FIGS. 3A and 3B). In addition, the tumor weight of the PAA treatment group was less than control group not treated with PAA, and was similar to that of doxorubicin as a positive control group (FIG. 3C). However, the body weight of mice in the PAA treatment group was similar to that of the control group (FIG. 3A). These results mean that PAA effectively inhibits generation of tumors in the xenograft tumor model.

Test Example 3: PAA Inhibits Breast Cancer Stem Cells

In order to identify whether or not PAA can inhibit formation of tumorspheres, primary mammospheres derived from MCF-7 and MDA-MB-231 cells were treated with different concentrations of PAA. As shown in FIG. 4, PAA inhibited formation of primary mammospheres derived from the breast cancer cell lines. The number of mammospheres derived from MCF-7 cells was decreased to 50 to 90% and the size of mammospheres was reduced (FIG. 4A). In addition, treatment with PAA reduced the number of primary mammospheres derived from MDA-MB-231 cells (FIG. 4B).

Figure 5A:
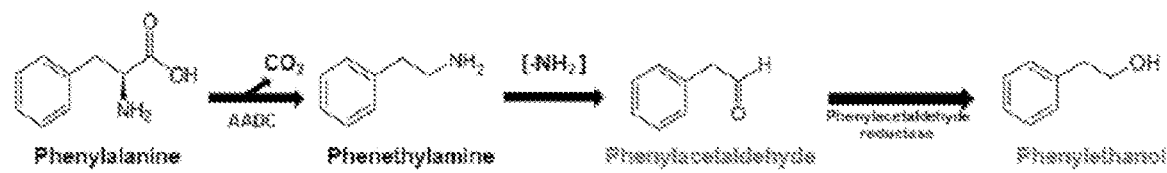

Then, formation of CSCs was analyzed by emission of PAA scent (FIG. 4C). As a result, PAA inhibited formation of CSCs. Volatile materials, i.e., PAA and phenylethanol, which are the most important for roses and tomatoes were derived from phenylalanine, as shown in FIG. 5A (FIG. 5A). In order to investigate whether or not phenylalanine-derived volatile materials, i.e., PAA and phenylethanol, and structural analogs (2- and 3-phenylpropionaldehydes) can inhibit formation of tumorspheres, these volatile materials were exposed to MCF-7. As a result, as shown in FIG. 5B, PAA and 2-phenylpropionaldehyde potently inhibited formation of primary mammospheres derived from MCF-7 cells. In addition, 3-phenylpropionaldehyde and phenylethanol also inhibited formation of primary mammospheres.

Test Example 4: PAA Reduces the Ratio of Populations Expressing $CD44^{high}/CD24^{low}$ and ALDH Positive Breast Cancer Cells MDA-MB-231 cells were treated with PAA for 24 hours and effects of the PAA inhibitor on the subpopulation expressing $CD44^{high}/CD24^{low}$ in breast cancer cells were investigated. As a result, the PAA inhibitor reduced the subpopulation expressing $CD44^{high}/CD24^{low}$ in breast cancer cells (FIG. 6A). MDA-MB-231 cells were treated with PAA for hours and ALDEFLUOR assay was conducted in order to investigate effects of PAA inhibitor on the proportion of ALDH-positive breast cancer cells. As a result, the PAA inhibitor reduced the proportion of ALDH-positive breast cancer cells to a level of 0.9% to 0.1% (FIG. 6B).

Figure 7A:
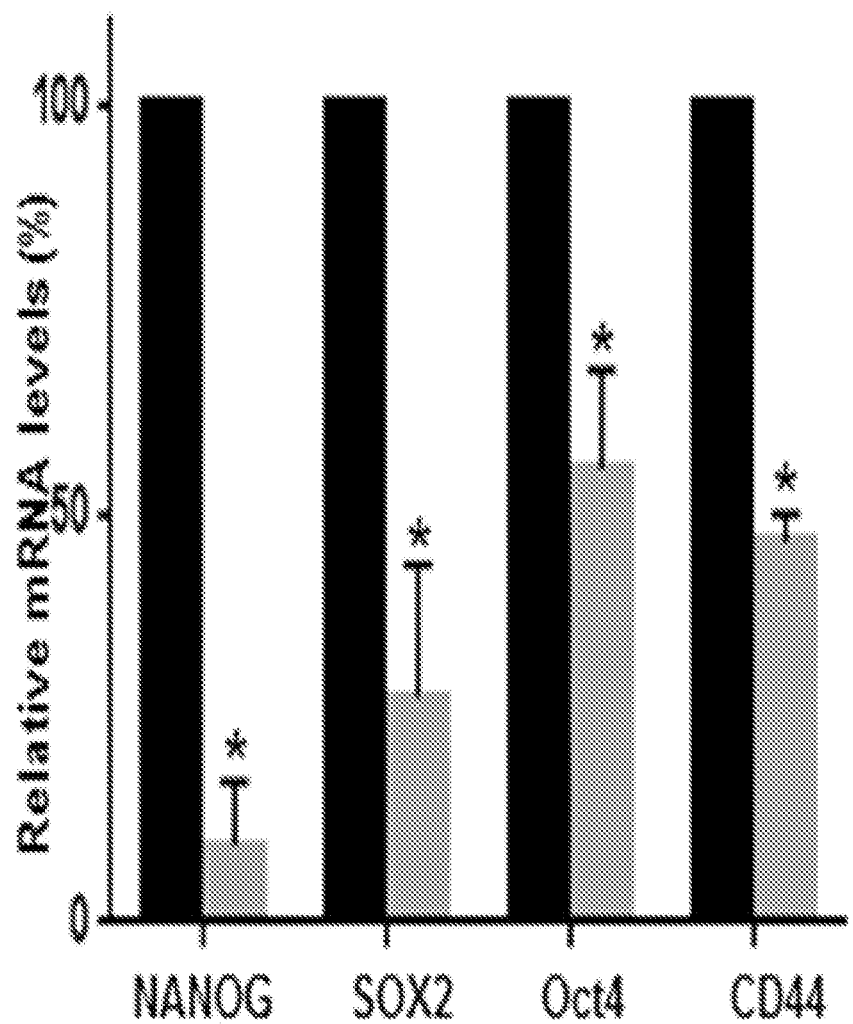

Test Example 5: PAA Inhibits Expression of Self-Renewal Genes of Cancer Stem Cells (CSCs) and Proliferation of Mammospheres In order to identify whether or not PAA inhibits expression of self-renewal genes, expression of self-renewal genes was investigated by real-time PCR. As a result, PAA reduced expression of self-renewal genes such as Nanog, Sox2, Oct4, and CD44 in breast cancer cells (FIG. 7A).

In general, it is known that increased ROSs kill cancer stem cells (CSCs) and low ROSs relate to stemness of stem cells and cancer stem cells (CSCs) (Shi X, Zhang Y, Zheng J and Pan J. Reactive oxygen species in cancer stem cells. Antioxid Redox Signal. 2012; 16(11):1215-1228).

Figure 7B:
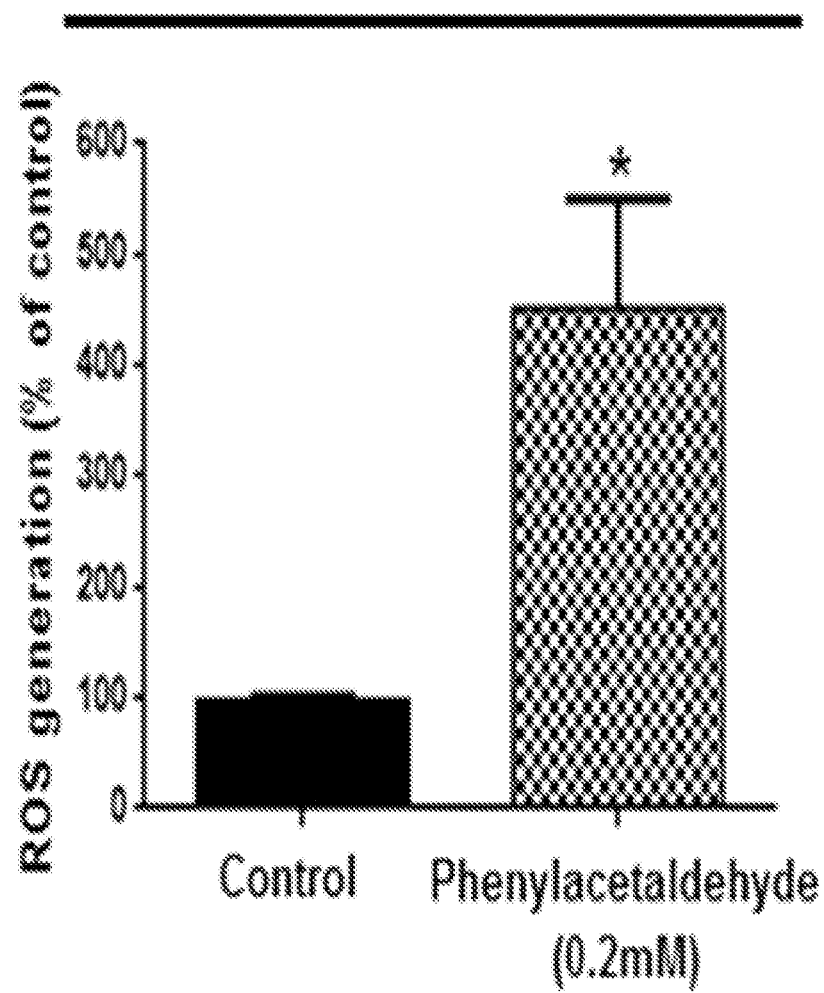

Accordingly, for PAA, the levels of ROSs in breast cancer stem cells were investigated. As a result, PAA induced ROS activity in MDA-MB-231 cells (FIG. 7B). Next, in order to identify whether or not PAA inhibits proliferation of mammospheres, the mammospheres were treated with PAA and the cell number of mammospheres was counted. As a result, PAA induced apoptosis of mammospheres and the number of cells observed in PAA-treated mammospheres was small. These results indicated that PAA greatly reduces proliferation of mammospheres (FIG. 7C).

Test Example 6: PAA Inhibits STAT3 Signaling and IL-6 Secretion in Mammospheres

In order to investigate cellular functions of PAA, STAT3 and NF-κB pathways were investigated in MCF-7-derived mammospheres subjected to treatment with PAA. As compared to the control group, PAA reduced phosphorylation of nuclear STAT3 proteins. However, PAA did not reduce protein levels of nuclear p65 (FIG. 8A).

In addition, bonding between PAA-treated nuclear extracts and Stat3 DNAs was analyzed using a biotin-labelled Stat-conjugated probe that bonds to STAT3 at a high affinity. As shown in FIG. 8B, PAA inhibited bonding between biotin-labelled Stat probe and Stat3 (FIG. 8B, lane 3). The specificity of pStat3/biotin-labelled Stat3 probe was identified using an unlabeled excess self-competitor (FIG. 8B, lane 4) and a mutated-Stat competitor (FIG. 8B, lane 5). It can be seen through such data that STAT3 signaling pathways are important for growth of mammospheres and regulation of self-renewal, and PAA inhibits self-renewal of mammospheres through STAT3 signaling.

The secreted IL-6 is known to play a key role in the formation of mammospheres (Sansone P, Storci G, Tavolari S, Guarnieri T, Giovannini C, Taffurelli M, Ceccarelli C, Santini D, Paterini P, Marcu K B, Chieco P and Bonafe M. IL-6 triggers malignant features in mammospheres from human ductal breast carcinoma and normal mammary gland. J Clin Invest. 2007; 117(12):3988-4002). Accordingly, in order to investigate the amount of produced secreted IL-6, western blot analysis was conducted in a culture solution of mammospheres using IL-6 antibodies. As a result, as shown in FIG. 8C, after treatment with PAA, the production level of secreted IL-6 was reduced. The internal control group was used to count mammospheres before and after treatment with PAA.

Test Example 7: Phenylacetaldehyde (PAA) Inhibits Neither Apoptosis nor Proliferation of Human Colorectal Cells Next, in order to investigate anti-proliferation effects of PAA on human colorectal cancer cell lines, i.e., HT-29 cells, after treatment with PAA at different concentrations, MTS analysis was conducted. As a result, even treatment with PAA did not affect growth of colorectal cancer cells (FIG. 9).

Accordingly, the PAA of the present invention has no inhibitory effects against colorectal cancer and inhibits growth of breast cancer and breast cancer stem cells, which means that PAA has a growth inhibition effect specific to breast cancer and breast cancer stem cells.

The present invention described above was completed based on the support of CK-1 (University for Creative Korea project).

Those skilled in the field to which the present invention pertains will appreciate that the present invention can be implemented in other specific embodiments while not changing the technical scope or indispensable features. In this regard, it should be understood that the aforementioned embodiments are exemplary and not limited in all respects. It should be understood that all alterations and modifications derived from the meaning and scope of the following claims and equivalent concepts thereof, rather than the Detailed Description of the Invention, fall into the scope of the present invention.

The invention claimed is:

1. A method of inhibiting breast cancer tumor growth, comprising direct intratumoral injection of 10 mg/kg to 50 mg/kg phenylacetaldehyde to mice bearing breast cancer tumors a composition.

* * * * *